(12) United States Patent
Tsai et al.

(10) Patent No.: US 12,258,402 B2
(45) Date of Patent: Mar. 25, 2025

(54) ANTIBODY SPECIFIC TO NECTIN CELL ADHESION MOLECULE 4 AND USES THEREOF

(71) Applicant: NAVI BIO-THERAPEUTICS, INC., Kaohsiung (TW)

(72) Inventors: Bor-Yu Tsai, New Taipei (TW); Shin-Tsung Huang, Taipei (TW); Wei-Ting Hsu, Taipei (TW)

(73) Assignee: NAVI BIO-THERAPEUTICS, INC., Kaohsiung (TW)

( * ) Notice: Subject to any disclaimer, the term of this patent is extended or adjusted under 35 U.S.C. 154(b) by 149 days.

(21) Appl. No.: 18/153,993

(22) Filed: Jan. 12, 2023

(65) Prior Publication Data

US 2023/0220078 A1     Jul. 13, 2023

Related U.S. Application Data

(60) Provisional application No. 63/266,711, filed on Jan. 12, 2022.

(51) Int. Cl.
| | |
|---|---|
| *C07K 16/28* | (2006.01) |
| *A61K 39/00* | (2006.01) |
| *A61K 47/68* | (2017.01) |
| *A61P 35/00* | (2006.01) |

(52) U.S. Cl.
CPC ...... *C07K 16/2803* (2013.01); *A61K 47/6849* (2017.08); *A61P 35/00* (2018.01); *A61K 39/00* (2013.01)

(58) Field of Classification Search
None
See application file for complete search history.

(56) References Cited

U.S. PATENT DOCUMENTS

| | | |
|---|---|---|
| 2020/0231670 A1 | 7/2020 | Morrison et al. |
| 2021/0130459 A1 | 5/2021 | Mandelboim et al. |
| 2021/0275683 A1 | 9/2021 | Baum et al. |
| 2021/0324104 A1 | 10/2021 | Lopez |

FOREIGN PATENT DOCUMENTS

| | | | |
|---|---|---|---|
| CN | 114478780 A | * | 5/2022 |
| TW | 201902922 A | | 1/2019 |
| WO | 2021069508 A1 | | 4/2021 |
| WO | 20211257525 A1 | | 12/2021 |
| WO | 2023137398 A2 | | 7/2023 |

OTHER PUBLICATIONS

Office Action issued on Jan. 31, 2024 in Taiwan Patent Application No. 112101454. English translation of Search Report included.
International Search Report and Written Opinion issued on Jul. 18, 2023, in International Patent Application No. PCT/US2023/060588.

\* cited by examiner

*Primary Examiner* — Amy E Juedes
*Assistant Examiner* — Maureen Varina Driscoll
(74) *Attorney, Agent, or Firm* — Prosyla Group PC

(57) ABSTRACT

The present disclosure relates to a modified antibody, or antigen-binding fragment thereof, specific for nectin cell adhesion molecule 4 (nectin-4). The present disclosure also relates to a method of detecting or diagnosing whether a subject has, or is at risk of developing a tumor, or assessing a prognosis of a tumor and a pharmaceutical composition for use in treating, prophylactic treating and/or preventing tumor in a subject afflicted with the tumor.

14 Claims, 14 Drawing Sheets
Specification includes a Sequence Listing.

| | ←------FR1------→ | ←CDR1-→ | ←-----FR2----→ | ←CDR2-→ | ←----------FR3----------→ | ←--CDR3--→ | ←--FR4--→ |
|---|---|---|---|---|---|---|---|
| Chicken scFv | ALTQPSSVSANPGGTVKITC | SGDSS--YYG | WYQQKAPGSAPVTVIY | DMTNRPS | NIPSRFSGSKSGSTATLTITGVRADDNAVYYC | ASTDSSS--TAGI | FGAGTTLTVL |
| NECTIN4-scFv-L1 | ALTQPSSVSANPGETVKITC | SGGSSNYYG | WYQQKSPGSAPVTLIY | NNNKRPS | DIPSRFSASKSGSTHTLTITGVRAEDEAVYFC | GGWDKSA---GI | FGAGTTLTVL |
| NECTIN4-scFv-S2 | ALTQPSSVSANPGETVEVTC | SGDDSRYYG | WYQQKSPGSAPVTVIY | YNDKRPS | DIPSRFSGSKSGSTGTLTITGVQAEDEAVYFC | GAYDSTTHSGSA | FGAGTTLTVL |
| NECTIN4-scFv-S6 | ALTQPSSVSTNLGETVEITC | SGSSGYGYG | WYQQKSPGSAPVTVIY | SNDKRPS | DIPSRFSGSASGSTATLTITGVRAEDEAVYLC | GGYDSSASYVGI | FGAGTTLTVL |
| NECTIN4-scFv-S8 | ALTQPSSVSANLGGTVEITC | SGGSGYGYG | WYQQKSPGSAPVTVIY | SNDKRPS | DIPSRFSGSASGSTATLTITGVRAEDEAVYFC | GGYDSSASYVGI | FGAGTTLTVL |
| NECTIN4-scFv-S21 | ALTQPSSVSANLGGTVKITC | SGGSG-SYG | WYQQKSPGSAPVTLIY | ANTNRPS | DIPSRFSGGSKSGSTSTLTITGVQAEDVAVYYC | GSRDSS--YVGI | FGAGTTLTVL |

FIG. 2A

| | FR1 | CDR1 | FR2 |
|---|---|---|---|
| Chicken scFv | AVTLDESGGGLQTPGGALRLVCKASGFTFS | SYDML | WRQAPGKGLEFVA |
| NECTIN4-scFv-L1 | AVTLDESGGGLQAPGGGLSLVCRASGFTFS | SHGMF | WVRQAPGKGLEFVA |
| NECTIN4-scFv-S2 | TVTLDESGGGLQTPGGGLSLVCKGSGFTFS | SNGMA | WVRQAPGKGLEFVG |
| NECTIN4-scFv-S6 | TVTLDESGGGLQTPGGGLSLVCKGSGFTFS | SNGMA | WVRQAPGKGLEFVA |
| NECTIN4-scFv-S8 | TVTLDESGGGLQTPGGGLSLVCKASGFTFN | DYGMG | WMRQAPGKGLEWVA |
| NECTIN4-scFv-S21 | AVTLDESGGGLQTPGGALSLVCKASGFTFS | SYAMM | WVRQAPGKGLEYIA |

| | CDR2 | FR3 |
|---|---|---|
| Chicken scFv | GIDNTGSYTHYGAAVKG | RATISRDNGQSTGRLQLNNLRAEDTATYYC |
| NECTIN4-scFv-L1 | GISDAGSWTGYGAAVKG | RATISRDSGQSTVRLQLNDLRAEDTGIYYC |
| NECTIN4-scFv-S2 | GVNAAGSWTGYGAAVKG | RATISRDNGQSTVRLQLNDLRAEDTGTYYC |
| NECTIN4-scFv-S6 | GVNAAGSWTGYGAAVKG | RATISRDNGQSTVRLQLNDLRAEDTGTYYC |
| NECTIN4-scFv-S8 | GISGSGSYTDYGAAVKG | RAIISRDNGQSTVRLQLNNLRAEDTGTYYC |
| NECTIN4-scFv-S21 | GIRSDGRYTYYGAAVKG | RATISRDNGQSTVRLQLNNLRAEDTGTYYC |

| | CDR3 | FR4 |
|---|---|---|
| Chicken scFv | AK------------RTAGS | IDAWGHTEVIVSS |
| NECTIN4-scFv-L1 | AK--------SAGDWY-GADD | IDAWGHTEVIVSS |
| NECTIN4-scFv-S2 | AK--------TADDWY-GADD | IDAWGHTDVIVSS |
| NECTIN4-scFv-S6 | AK--------TADDWY-GADD | IDAWGHTEVIVSS |
| NECTIN4-scFv-S8 | AK--------GSNSAYPDAAD | IDAWGHTEVIVSS |
| NECTIN4-scFv-S21 | AKSGVTDTSSSTYSSASN | IDAWGHTEVIVSS |

FIG. 2B

ANTIBODY SPECIFIC TO NECTIN CELL ADHESION MOLECULE 4 AND USES THEREOF

PRIORITY INFORMATION

The subject application claims priority to and benefit of U.S. Provisional Patent Application No. 63/266,711, filed Jan. 12, 2022, the content of which is incorporated herein by reference in its entirety.

SEQUENCE LISTING

The instant application contains a Sequence Listing which is submitted electronically in .xml format and is hereby incorporated by reference in its entirety. The .xml copy, created on Jan. 12, 2023, is named "G4590-15400US_SeqListing_20230112.xml" and is 45 kilobytes in size.

FIELD OF THE DISCLOSURE

The present disclosure relates to an antibody or antigen-binding fragment thereof, which is specific to nectin cell adhesion molecule 4 (nectin-4) for detecting and/or treating a tumor.

BACKGROUND OF THE DISCLOSURE

Cancer is among the leading causes of death worldwide. Cancer mortality can be reduced if cases are detected and treated early, so there is a push to have viable screening options for the general population.

Immunotherapy is one of the most promising advancements in cancer treatment. Cancer immunotherapy is utilized for generating and augmenting an anti-tumor immune response, e.g., by treatment with antibodies specific to antigens on tumor cells, with fusions of antigen presenting cells with tumor cells, or by activation of anti-tumor T cells. The ability to recruit immune cells (e.g., T cells) against tumor cells in a patient provides a therapeutic modality of fighting cancer types and metastasis that until recently were considered incurable.

Survival rates are dramatically improved when carcinomas are diagnosed early and the disease is limited to the organ of origin. Indeed, physical methods for screening like pap smears in cervical cancer and mammography in breast cancer have dramatically reduced mortality rates. Thus, research on developing new early detection biomarkers in easily accessible body fluids, such as serum, urine or saliva has been encouraged. Some well-known biomarkers are reliably detected in advanced stages of disease, but lack sufficient sensitivity and especially specificity for early cancer diagnosis, and are thus used mainly for prognosis, staging, monitoring and selection of therapy.

Thus, there is a need for developing a novel approach to treatment and detection of cancer.

SUMMARY OF THE DISCLOSURE

The present disclosure provides an antibody or antigen-binding fragment thereof that specifically binds to an epitope on an antigen or a fragment thereof for treatment and detection of cancer.

In one aspect, the present disclosure provides an antibody or antigen-binding fragment thereof specific for an epitope on nectin cell adhesion molecule 4 or a fragment thereof; which comprises complementarity determining regions (CDRs) of a heavy chain variable region and CDRs of a light chain variable region, wherein the CDRs of the heavy chain variable region comprises CDRH1, CDRH2 and CDRH3 regions, and the CDRs of the light chain variable region comprises CDRL1, CDRL2 and CDRL3 regions, and wherein: the CDRH1 region comprises an amino acid sequence selected from the group consisting of SEQ ID NOs: 2 to 6 or a substantially similar sequence having at least 90% sequence identity; the CDRH2 region comprises an amino acid sequence selected from the group consisting of SEQ ID NOs: 8 to 12 or a substantially similar sequence having at least 90% sequence identity; the CDRH3 region comprises an amino acid sequence selected from the group consisting of SEQ ID NOs: 14 to 18 or a substantially similar sequence having at least 90% sequence identity; and the CDRL1 region comprises an amino acid sequence selected from the group consisting of SEQ ID NOs: 20 to 24 or a substantially similar sequence having at least 90% sequence identity; the CDRL2 region comprises an amino acid sequence selected from the group consisting of SEQ ID NOs: 26 to 30 or a substantially similar sequence having at least 90% sequence identity; the CDRL3 region comprises an amino acid sequence selected from the group consisting of SEQ ID NOs: 32 to 36 or a substantially similar sequence having at least 90% sequence identity.

In one embodiment of the disclosure, nectin-4 is human nectin-4.

In some embodiments of the disclosure, the antibody or antigen-binding fragment thereof is specific for an epitope on an extracellular domain of nectin-4 or the fragment thereof; examples of the nectin-4 fragment include, but are not limited to, amino acids 94 to 435, 94 to 732 or 94 to 957 of nectin-4-Q96NY8 (PVRL4_HUMAN).

In one embodiment of the disclosure, the antibody NECTIN4-scFv-L1 or antigen-binding fragment thereof comprises the CDRH1 region comprising SEQ ID NO: 2 or a substantially similar sequence having at least 90% sequence identity, the CDRH2 region comprising SEQ ID NO: 8 or a substantially similar sequence having at least 90% sequence identity, the CDRH3 region comprising SEQ ID NO: 14 or a substantially similar sequence having at least 90% sequence identity, the CDRL1 region comprising SEQ ID NO: 20 or a substantially similar sequence having at least 90% sequence identity, the CDRL2 region comprising SEQ ID NO: 26 or a substantially similar sequence having at least 90% sequence identity, and the CDRL3 region comprising SEQ ID NO: 32 or a substantially similar sequence having at least 90% sequence identity. In one embodiment, the heavy chain variable region comprises an amino acid sequence of SEQ ID NO: 37 or a substantially similar sequence having at least 90% sequence identity; and the light chain variable region comprises an amino acid sequence of SEQ ID NO: 38 or a substantially similar sequence having at least 90% sequence identity.

In one embodiment of the disclosure, the antibody NECTIN4-scFv-S2 or antigen-binding fragment thereof comprises the CDRH1 region comprising SEQ ID NO: 3 or a substantially similar sequence having at least 90% sequence identity, the CDRH2 region comprising SEQ ID NO: 9 or a substantially similar sequence having at least 90% sequence identity, the CDRH3 region comprising SEQ ID NO: 15 or a substantially similar sequence having at least 90% sequence identity, the CDRL1 region comprising SEQ ID NO: 21 or a substantially similar sequence having at least 90% sequence identity, the CDRL2 region comprising SEQ ID NO: 27 or a substantially similar sequence having at least 90% sequence identity, and the CDRL3 region comprising SEQ ID NO: 33 or a substantially similar sequence having at least 90% sequence identity. In one embodiment, the heavy chain variable region comprises an amino acid sequence of SEQ ID NO: 39 or a substantially similar sequence thereof; and the light chain variable region comprises an amino acid sequence of SEQ ID NO: 40 or a substantially similar sequence thereof.

In one embodiment of the disclosure, the antibody NEC-TIN4-scFv-S6 or antigen-binding fragment thereof comprises the CDRH1 region comprising SEQ ID NO: 4 or a substantially similar sequence having at least 90% sequence identity, the CDRH2 region comprising SEQ ID NO: 10 or a substantially similar sequence having at least 90% sequence identity, the CDRH3 region comprising SEQ ID NO: 16 or a substantially similar sequence having at least 90% sequence identity, the CDRL1 region comprising SEQ ID NO: 22 or a substantially similar sequence having at least 90% sequence identity, the CDRL2 region comprising SEQ ID NO: 28 or a substantially similar sequence having at least 90% sequence identity, and the CDRL3 region comprising SEQ ID NO: 34 or a substantially similar sequence having at least 90% sequence identity. In one embodiment, the heavy chain variable region comprises an amino acid sequence of SEQ ID NO: 41 or a substantially similar sequence having at least 90% sequence identity; and the light chain variable region comprises an amino acid sequence of SEQ ID NO: 42 or a substantially similar sequence having at least 90% sequence identity.

In one embodiment of the disclosure, the antibody NEC-TIN4-scFv-S8 or antigen-binding fragment thereof comprises the CDRH1 region comprising SEQ ID NO: 5 or a substantially similar sequence having at least 90% sequence identity, the CDRH2 region comprising SEQ ID NO: 11 or a substantially similar sequence having at least 90% sequence identity, the CDRH3 region comprising SEQ ID NO: 17 or a substantially similar sequence having at least 90% sequence identity, the CDRL1 region comprising SEQ ID NO: 23 or a substantially similar sequence having at least 90% sequence identity, the CDRL2 region comprising SEQ ID NO: 29 or a substantially similar sequence having at least 90% sequence identity, and the CDRL3 region comprising SEQ ID NO: 35 or a substantially similar sequence having at least 90% sequence identity. In one embodiment, the heavy chain variable region comprises an amino acid sequence of SEQ ID NO: 43 or a substantially similar sequence having at least 90% sequence identity; and the light chain variable region comprises an amino acid sequence of SEQ ID NO: 44 or a substantially similar sequence having at least 90% sequence identity.

In one embodiment of the disclosure, the antibody NEC-TIN4-scFv-S21 or antigen-binding fragment thereof comprises the CDRH1 region comprising SEQ ID NO: 6 or a substantially similar sequence having at least 90% sequence identity, the CDRH2 region comprising SEQ ID NO: 12 or a substantially similar sequence having at least 90% sequence identity, the CDRH3 region comprising SEQ ID NO: 18 or a substantially similar sequence having at least 90% sequence identity, the CDRL1 region comprising SEQ ID NO: 24 or a substantially similar sequence having at least 90% sequence identity, the CDRL2 region comprising SEQ ID NO: 30 or a substantially similar sequence having at least 90% sequence identity, and the CDRL3 region comprising SEQ ID NO: 36 or a substantially similar sequence having at least 90% sequence identity. In one embodiment, the heavy chain variable region comprises an amino acid sequence of SEQ ID NO: 45 or a substantially similar sequence thereof; and the light chain variable region comprises an amino acid sequence of SEQ ID NO: 46 or a substantially similar sequence thereof.

In some embodiments of the disclosure, the antibody or a fragment thereof is a monoclonal antibody, chimeric antibody, humanized antibody, human antibody or scFv antibody or a fragment thereof.

In some embodiments of the disclosure, the antibody or antigen-binding fragment thereof is conjugated with a therapeutic agent. Examples of the therapeutic agent include, but are not limited to, antimetabolites, alkylating agents, alkylating-like agents, DNA minor groove alkylating agents, anthracyclines, antibiotics, calicheamicins, antimitotic agents, topoisomerase inhibitors, HDAC inhibitor, proteasome inhibitors, and radioisotopes.

In some embodiments of the disclosure, the antibody or antigen-binding fragment thereof is expressed on a surface of a cell. The cell may be an immune cell, a cancer stem cell or a stem cell. In one embodiment of the disclosure, the immune cell is a T cell.

The present disclosure also provides a vector encoding the antibody or antigen-binding fragment thereof.

The present disclosure also provides a genetically engineered cell expressing the antibody or antigen-binding fragment thereof or containing the vector.

The present disclosure still also provides a pharmaceutical composition comprising an effective amount of the antibody or antigen-binding fragment thereof or the genetically engineered cell.

In another aspect, the present disclosure provides a method of detecting or diagnosing whether a subject has, or is at risk of developing a tumor, or assessing a prognosis of a tumor, comprising contacting a sample derived from the subject with the antibody or antigen-binding fragment thereof.

The present disclosure provides a method for detecting nectin-4 in a sample comprising contacting the sample with the antibody or antigen-binding fragment thereof.

The present disclosure also provides a kit for detecting nectin-4 in a sample, wherein the kit comprises the antibody or antigen-binding fragment thereof.

In another aspect, the present disclosure provides a method for treating, prophylactic treating and/or preventing a tumor in a subject afflicted with the tumor, comprising administering to the subject the pharmaceutical composition. Alternatively, the present disclosure provides a pharmaceutical composition for use in treating, prophylactic treating and/or preventing a tumor in a subject afflicted with the tumor, comprising an effective amount of the antibody or antigen-binding fragment thereof or the genetically engineered cell as disclosed herein. Examples of the tumor include, but are not limited to, squamous cell cancer, lung cancer, cancer of the peritoneum, hepatocellular cancer, gastric or stomach cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma, head and neck cancer, B-cell lymphoma, chronic lymphocytic leukemia (CLL), acute lymphoblastic leukemia (ALL), Hairy cell leukemia, and chronic myeloblastic leukemia. Particularly, the tumor is triple negative breast cancer, bladder cancer, lung cancer, pancreatic cancer, ovarian cancer, head/neck cancer or esophageal cancer.

The present disclosure is described in detail in the following sections. Other characteristics, purposes and advantages of the present disclosure can be found in the detailed description and claims.

BRIEF DESCRIPTION OF DRAWINGS

FIG. 2A shows scFv sequence alignment of light chain variable regions of chicken immunoglobulin. FIG. 2B shows scFv sequence alignment of heavy chain variable regions of chicken immunoglobulin.

FIG. 9A: MCF7; FIG. 9B: MCF10A.

DETAILED DESCRIPTION OF THE DISCLOSURE

Figure 1:
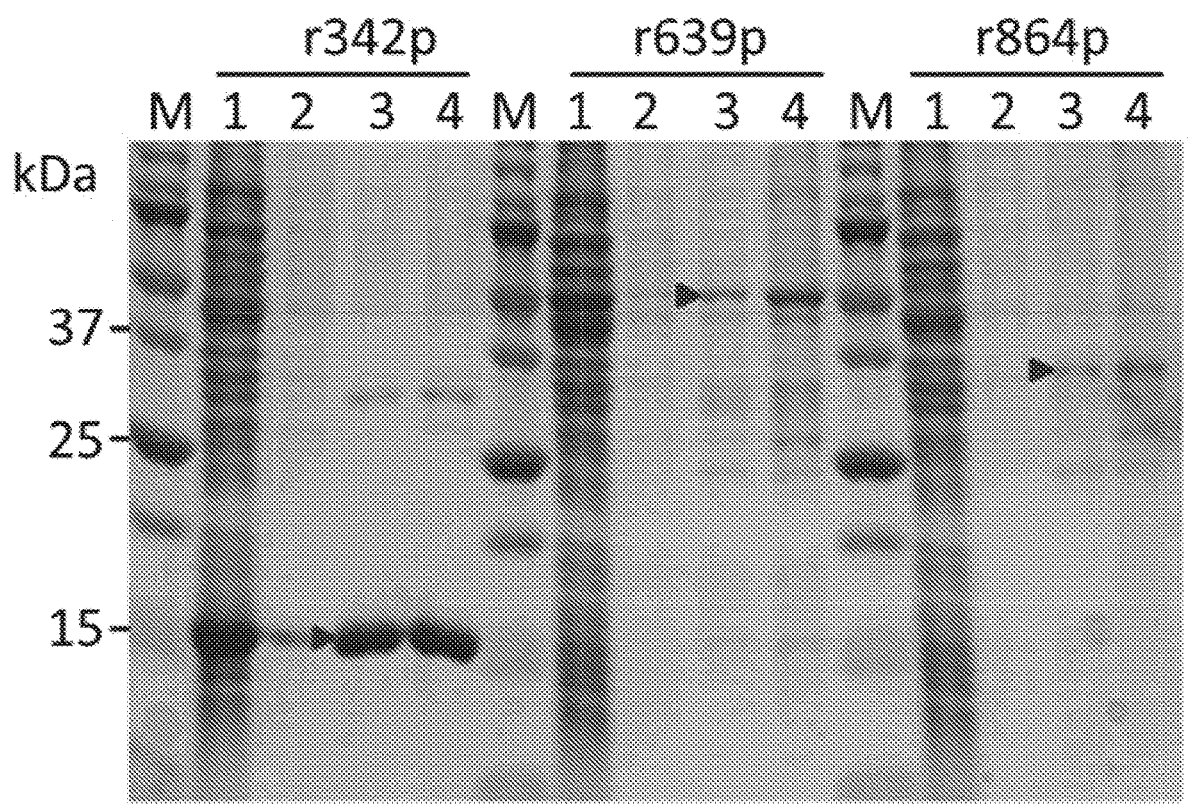
FIG. 1 shows expression of PVRL4 fragments in Example 1. Lane 1: supernatant after $Ni^+$ sepharose binding; Lane 2: collected washing buffer; Lane 3: collected elution buffer (imidazole); Lane 4: $Ni^+$ sepharose after elution. Predicted size: r342p: 15 kDa; r639p: 48 kDa; r864p: 34 kDa.

In the description that follows, a number of terms are used and the following definitions are provided to facilitate understanding of the claimed subject matter. Terms that are not expressly defined herein are used in accordance with their plain and ordinary meanings.

Unless otherwise specified, "a" or "an" means "one or more."

As used herein, the term "epitope" refers to the site on the antigen to which an antibody binds.

The term "antibody," as used herein, means any antigen-binding molecule or molecular complex comprising at least one complementarity determining region (CDR) that specifically binds to or interacts with a particular antigen (e.g., nectin-4). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_{H1}$, $C_{H2}$ and $C_{H3}$. Each light chain comprises a light chain variable region (abbreviated herein as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-nectin-4 antibody (or antigen-binding portion thereof) may be identical to the human germline sequences, or may be naturally or artificially modified. An amino acid consensus sequence may be defined based on a side-by-side analysis of two or more CDRs.

As used herein, the term "being specific" means that an antibody does not cross react to a significant extent with other epitopes.

As used herein, the term "complementarity determining region" (CDR) refers to the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other.

As applied to polypeptides, the term "substantial similarity" or "substantially similar" means that two peptide sequences, when optimally aligned, such as by the programs GAP or BESTFIT using default gap weights, share at least 90%, 91%, 92%, 93%, 94%, 95%, 96%, 97%, 98% or 99% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

The term "monoclonal antibody" as used herein is not limited to antibodies produced through hybridoma technology. A monoclonal antibody is derived from a single clone, including any eukaryotic, prokaryotic, or phage clone, by any means available or known in the art.

The term "chimeric" antibody as used herein refers to an antibody having variable sequences derived from a non-human immunoglobulin and human immunoglobulin constant regions, typically chosen from a human immunoglobulin template.

"Humanized" forms of non-human antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin, and all or substantially all of the FR regions are those of a human immunoglobulin sequence.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex.

As used in the present disclosure, the term "therapeutic agent" means any compound, substance, drug, prodrug or active ingredient having a therapeutic or pharmacological effect that is suitable for administration to a mammal, for example a human.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "genetically engineered" cells or "genetic engineering" of cells means manipulating genes using genetic materials for the change of gene copies and/or gene expression level in the cell. The genetic materials can be in the form of DNA or RNA. The genetic materials can be transferred into cells by various means including viral transduction and non-viral transfection. After being genetically engineered, the expression level of certain genes in the cells can be altered permanently or temporarily.

As used in the present disclosure, the term "pharmaceutical composition" means a mixture containing a therapeutic agent administered to a mammal, for example a human, for preventing, treating, or eliminating a particular disease or pathological condition that the mammal suffers.

As used herein, the term "therapeutically effective amount" or "efficacious amount" refers to the amount of an antibody that, when administered to a mammal or other subject for treating a disease, is sufficient to effect such treatment for the disease.

As used herein, the terms "treatment," "treating," and the like, cover any treatment of a disease in a mammal, particularly in a human, and include: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The term "preventing" or "prevention" is recognized in the art, and when used in relation to a condition, it includes administering, prior to onset of the condition, an agent to reduce the frequency or severity of or to delay the onset of symptoms of a medical condition in a subject, relative to a subject which does not receive the agent.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, the term "in need of treatment" refers to a judgment made by a caregiver (e.g., physician, nurse, nurse practitioner, or individual in the case of humans; veterinarian in the case of animals, including non-human mammals) that a subject requires or will benefit from treatment. This judgment is made based on a variety of factors that are in the realm of a caregiver's expertise, but that includes the knowledge that the subject is ill, or will be ill, as the result of a condition that is treatable by the compounds of the present disclosure.

"Cancer," "tumor," and like terms include precancerous, neoplastic, transformed, and cancerous cells, and can refer to a solid tumor, or a non-solid cancer (see, e.g., Edge et al. AJCC Cancer Staging Manual (7th ed. 2009); Cibas and Ducatman Cytology: Diagnostic principles and clinical correlates (3rd ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, Culture of Animal Cells a Manual of Basic Technique (3rd ed. 1994)). Although transformation can arise from infection with a transforming virus and incorporation of new genomic DNA, or uptake of exogenous DNA, it can also arise spontaneously or following exposure to a carcinogen.

As used herein, the term "sample" encompasses a variety of sample types obtained from an individual, subject or patient which can be used in a diagnostic or monitoring assay. The definition encompasses blood and other liquid samples of biological origin, solid tissue samples such as a biopsy specimen or tissue cultures or cells derived therefrom and the progeny thereof.

The present disclosure provides an antibody or antigen-binding fragment thereof that specifically binds to an epitope on nectin-4 or a fragment thereof.

In one embodiment, the antibody or antigen-binding fragment thereof (anti-nectin-4) comprises complementarity determining regions (CDRs) of a heavy chain variable region and complementarity determining regions of a light chain variable region, wherein the complementarity determining regions of the heavy chain variable region comprise CDRH1, CDRH2 and CDRH3 regions, and the complementarity determining regions of the light chain variable region comprise CDRL1, CDRL2 and CDRL3 regions, and wherein:
the CDRH1 region comprises an amino acid sequence selected from the group consisting of SEQ ID NOs: 2 to 6 or a substantially similar sequence having at least 90%, at least 95%, at least 98% or at least 99% sequence identity; the CDRH2 region comprises an amino acid sequence selected from the group consisting of SEQ ID NOs: 8 to 12 or a substantially similar sequence having at least 90%, at least 95%, at least 98% or at least 99% sequence identity; the CDRH3 region comprises an amino acid sequence selected from the group consisting of SEQ ID NOs: 14 to 18 or a substantially similar sequence having at least 90%, at least 95%, at least 98% or at least 99% sequence identity; and the CDRL1 region comprises an amino acid sequence selected from the group consisting of SEQ ID NOs: 20 to 24 or a substantially similar sequence having at least 90%, at least 95%, at least 98% or at least 99% sequence identity; the CDRL2 region comprises an amino acid sequence selected from the group consisting of SEQ ID NOs: 26 to 30 or a substantially similar sequence having at least 90%, at least 95%, at least 98% or at least 99% sequence identity; the CDRL3 region comprises an amino acid sequence selected from the group consisting of SEQ ID NOs: 32 to 36 or a substantially similar sequence having at least 90%, at least 95%, at least 98% or at least 99% sequence identity.

Nectin cell adhesion molecule 4 (nectin-4), also known as poliovirus receptor related 4 (PVRL4), is a type I transmembrane protein and member of the nectin family of related immunoglobulin-like adhesion molecules. It is known that nectin-4 is located on the cell surface and able to bind with other cells or the extracellular matrix (ECM). In humans, nectin-4 mainly expresses during development at epithelial adhere junctions in trachea, lungs and skin (JBC 2001, 276(46):43205-43215). The expression declines in adult when the expression of other nectins continues in adult tissues. However, nectin-4 re-expresses as a tumor associated antigen with pro-oncogenic properties in various carcinomas including breast cancer. In tumors, nectin-4 and active form of ADAM17/TACE metalloprotease are overexpressed, and cleaved nectin-4 (soluble form) is observed in the cytoplasm (JBC 2005, 280(20):19543-50; BMC Cancer 2007, 7:73). Particularly, nectin-4 as disclosed herein is human nectin-4.

In some embodiments of the disclosure, the antibody or antigen-binding fragment thereof is specific for an epitope on an extracellular domain of nectin-4 or the fragment thereof; examples of the nectin-4 fragment include, but are not limited to, amino acids 94 to 435, 94 to 732 or 94 to 957 of nectin-4-Q96NY8 (PVRL4_HUMAN, NCBI Reference Sequence: NM_030916.3, UniProtKB/Swiss-Prot (Q96NY8.1)).

In one embodiment of the disclosure, the antibody NEC-TIN4-scFv-L1 or antigen-binding fragment thereof comprises the CDRH1 region comprising SEQ ID NO: 2 or a substantially similar sequence having at least 90%, at least 95%, at least 98% or at least 99% sequence identity, the CDRH2 region comprising SEQ ID NO: 8 or a substantially similar sequence having at least 90%, at least 95%, at least 98% or at least 99% sequence identity, the CDRH3 region comprising SEQ ID NO: 14 or a substantially similar sequence having at least 90%, at least 95%, at least 98% or at least 99% sequence identity, the CDRL1 region comprising SEQ ID NO: 20 or a substantially similar sequence having at least 90%, at least 95%, at least 98% or at least 99% sequence identity, the CDRL2 region comprising SEQ ID NO: 26 or a substantially similar sequence having at least 90%, at least 95%, at least 98% or at least 99% sequence identity, and the CDRL3 region comprising SEQ ID NO: 32 or a substantially similar sequence having at least 90%, at least 95%, at least 98% or at least 99% sequence identity. In one embodiment, the heavy chain variable region comprises the amino acid sequence of SEQ ID NO: 37 or a substantially similar sequence having at least 90%, at least 95%, at least 98% or at least 99% sequence identity; and the light chain variable region comprises the amino acid sequence of SEQ ID NO: 38 or a substantially similar sequence having at least 90%, at least 95%, at least 98% or at least 99% sequence identity.

In one embodiment of the disclosure, the antibody NEC-TIN4-scFv-S2 or antigen-binding fragment thereof comprises the CDRH1 region comprising SEQ ID NO: 3 or a substantially similar sequence having at least 90%, at least 95%, at least 98% or at least 99% sequence identity, the CDRH2 region comprising SEQ ID NO: 9 or a substantially similar sequence having at least 90%, at least 95%, at least 98% or at least 99% sequence identity, the CDRH3 region comprising SEQ ID NO: 15 or a substantially similar sequence having at least 90%, at least 95%, at least 98% or at least 99% sequence identity, the CDRL1 region comprising SEQ ID NO: 21 or a substantially similar sequence having at least 90%, at least 95%, at least 98% or at least 99% sequence identity, the CDRL2 region comprising SEQ ID NO: 27 or a substantially similar sequence having at least 90%, at least 95%, at least 98% or at least 99% sequence identity, and the CDRL3 region comprising SEQ ID NO: 33 or a substantially similar sequence having at least 90%, at least 95%, at least 98% or at least 99% sequence identity. In one embodiment, the heavy chain variable region comprises the amino acid sequence of SEQ ID NO: 39 or a substantially similar sequence having at least 90%, at least 95%, at least 98% or at least 99% sequence identity; and the light chain variable region comprises the amino acid sequence of SEQ ID NO: 40 or a substantially similar sequence having at least 90%, at least 95%, at least 98% or at least 99% sequence identity.

In one embodiment of the disclosure, the antibody NEC-TIN4-scFv-S6 or antigen-binding fragment thereof comprises the CDRH1 region comprising SEQ ID NO: 4 or a substantially similar sequence having at least 90%, at least 95%, at least 98% or at least 99% sequence identity, the CDRH2 region comprising SEQ ID NO: 10 or a substantially similar sequence having at least 90%, at least 95%, at least 98% or at least 99% sequence identity, the CDRH3 region comprising SEQ ID NO: 16 or a substantially similar sequence having at least 90%, at least 95%, at least 98% or at least 99% sequence identity, the CDRL1 region comprising SEQ ID NO: 22 or a substantially similar sequence having at least 90%, at least 95%, at least 98% or at least 99% sequence identity, the CDRL2 region comprising SEQ ID NO: 28 or a substantially similar sequence having at least 90%, at least 95%, at least 98% or at least 99% sequence identity, and the CDRL3 region comprising SEQ ID NO: 34 or a substantially similar sequence having at least 90%, at least 95%, at least 98% or at least 99% sequence identity. In one embodiment, the heavy chain variable region comprises the amino acid sequence of SEQ ID NO: 41 or a substantially similar sequence having at least 90%, at least 95%, at least 98% or at least 99% sequence identity; and the light chain variable region comprises the amino acid sequence of SEQ ID NO: 42 or a substantially similar sequence having at least 90%, at least 95%, at least 98% or at least 99% sequence identity.

In one embodiment of the disclosure, the antibody NEC-TIN4-scFv-S8 or antigen-binding fragment thereof comprises the CDRH1 region comprising SEQ ID NO: 5 or a substantially similar sequence having at least 90%, at least 95%, at least 98% or at least 99% sequence identity, the CDRH2 region comprising SEQ ID NO: 11 or a substantially similar sequence having at least 90%, at least 95%, at least 98% or at least 99% sequence identity, the CDRH3 region comprising SEQ ID NO: 17 or a substantially similar sequence having at least 90%, at least 95%, at least 98% or at least 99% sequence identity, the CDRL1 region comprising SEQ ID NO: 23 or a substantially similar sequence having at least 90%, at least 95%, at least 98% or at least 99% sequence identity, the CDRL2 region comprising SEQ ID NO: 29 or a substantially similar sequence having at least 90%, at least 95%, at least 98% or at least 99% sequence identity, and the CDRL3 region comprising SEQ ID NO: 35 or a substantially similar sequence having at least 90%, at least 95%, at least 98% or at least 99% sequence identity. In one embodiment, the heavy chain variable region comprises the amino acid sequence of SEQ ID NO: 43 or a substantially similar sequence having at least 90%, at least 95%, at least 98% or at least 99% sequence identity; and the light chain variable region comprises the amino acid sequence of SEQ ID NO: 44 or a substantially similar sequence having at least 90%, at least 95%, at least 98% or at least 99% sequence identity.

In one embodiment of the disclosure, the antibody NEC-TIN4-scFv-S21 or antigen-binding fragment thereof comprises the CDRH1 region comprising SEQ ID NO: 6 or a substantially similar sequence having at least 90%, at least 95%, at least 98% or at least 99% sequence identity, the CDRH2 region comprising SEQ ID NO: 12 or a substantially similar sequence having at least 90%, at least 95%, at least 98% or at least 99% sequence identity, the CDRH3 region comprising SEQ ID NO: 18 or a substantially similar sequence having at least 90%, at least 95%, at least 98% or at least 99% sequence identity, the CDRL1 region comprising SEQ ID NO: 24 or a substantially similar sequence having at least 90%, at least 95%, at least 98% or at least 99% sequence identity, the CDRL2 region comprising SEQ ID NO: 30 or a substantially similar sequence having at least 90%, at least 95%, at least 98% or at least 99% sequence identity, and the CDRL3 region comprising SEQ ID NO: 36 or a substantially similar sequence having at least 90%, at least 95%, at least 98% or at least 99% sequence identity. In one embodiment, the heavy chain variable region comprises the amino acid sequence of SEQ ID NO: 45 or a substantially similar sequence having at least 90%, at least 95%, at least 98% or at least 99% sequence identity; and the light chain variable region comprises the amino acid sequence of SEQ ID NO: 46 or a substantially similar sequence having at least 90%, at least 95%, at least 98% or at least 99% sequence identity.

The sequence listing is shown in Table 1.

TABLE 1

| SEQ ID NO | name | sequence |
| --- | --- | --- |
| 1 | Chicken scFv CDRH1 | SYDML |
| 2 | NECTIN4-scFv-L1 CDRH1 | SHGMF |
| 3 | NECTIN4-scFv-S2 CDRH1 | SNGMA |
| 4 | NECTIN4-scFv-S6 CDRH1 | SNGMA |
| 5 | NECTIN4-scFv-S8 CDRH1 | DYGMG |
| 6 | NECTIN4-scFv-S21 CDRH1 | SYAMM |
| 7 | Chicken scFv CDRH2 | GIDNTGSYTHYGAAVKG |
| 8 | NECTIN4-scFv-L1 CDRH2 | GISDAGSWTGYGAAVKG |
| 9 | NECTIN4-scFv-S2 CDRH2 | GVNAAGSWTGYGAAVKG |
| 10 | NECTIN4-scFv-S6 CDRH2 | GVNAAGSWTGYGAAVKG |
| 11 | NECTIN4-scFv-S8 CDRH2 | GISGSGSYTDYGAAVKG |
| 12 | NECTIN4-scFv-S21 CDRH2 | GIRSDGRYTYYGAAVKG |
| 13 | Chicken scFv CDRH3 | AK-----------RTAGS |
| 14 | NECTIN4-scFv-L1 CDRH3 | AK-----SAGDWY-GADD |
| 15 | NECTIN4-scFv-S2 CDRH3 | AK-----TADDWY-GADD |
| 16 | NECTIN4-scFv-S6 CDRH3 | AK-----TADDWY-GADD |
| 17 | NECTIN4-scFv-S8 CDRH3 | AK-----GSNSAYPDAAD |
| 18 | NECTIN4-scFv-S21 CDRH3 | AKSGVTDTSSSTYSSASN |

TABLE 1-continued

| SEQ ID NO | name | sequence |
|---|---|---|
| 19 | Chicken scFv CDRL1 | SGDSS-YYG |
| 20 | NECTIN4-scFv-L1 CDRL1 | SGGSSNYYG |
| 21 | NECTIN4-scFv-S2 CDRL1 | SGDDSRYYG |
| 22 | NECTIN4-scFv-S6 CDRL1 | SGSSGYGYG |
| 23 | NECTIN4-scFv-S8 CDRL1 | SGGSGYGYG |
| 24 | NECTIN4-scFv-S21 CDRL1 | SGGSG-SYG |
| 25 | Chicken scFv CDRL2 | DNTNRPS |
| 26 | NECTIN4-scFv-L1 CDRL2 | NNNKRPS |
| 27 | NECTIN4-scFv-S2 CDRL2 | YNDKRPS |
| 28 | NECTIN4-scFv-S6 CDRL2 | SNDKRPS |
| 29 | NECTIN4-scFv-S8 CDRL2 | SNDKRPS |
| 30 | NECTIN4-scFv-S21 CDRL2 | ANTNRPS |
| 31 | Chicken scFv CDRL3 | ASTDSSS-TAGI |
| 32 | NECTIN4-scFv-L1 CDRL3 | GGWDKSA---GI |
| 33 | NECTIN4-scFv-S2 CDRL3 | GAYDSTTHSGSA |
| 34 | NECTIN4-scFv-S6 CDRL3 | GGYDSSASYVGI |
| 35 | NECTIN4-scFv-S8 CDRL3 | GGYDSSASYVGI |
| 36 | NECTIN4-scFv-S21 CDRL3 | GSRDSS-YVGI |
| 37 | NECTIN4-scFv-L1 VH | AVTLDESGGGLQAPGGGLSLVCRASGFTFSSHGMFWVRQAPGKGLEFVA<br>GISDAGSWTGYGAAVKGRATISRDSGQSTVRLQLNNLRAEDTGIYYCAK<br>-----SAGDWY-GADDIDAWGHGTEVIVSS |
| 38 | NECTIN4-scFv-L1 VL | ALTQPSSVSANPGETVKITCSGGSSNYYGWYQQKSPGSAPVTLIYNNNK<br>RPSDIPSRFSASKSGSTHTLTITGVRAEDEAVYFCGGWDKSA---GIFG<br>AGTTLTVL |
| 39 | NECTIN4-scFv-S2 VH | TVTLDESGGGLQTPGGGLSLVCKGSGFTFSSNGMAWVRQAPGKGLEFVG<br>GVNAAGSWTGYGAAVKGRATISRDNGQSTVRLQLNDLRAEDTGTYYCAK<br>-----TADDWY-GADDIDAWGHGTEVIVSS |
| 40 | NECTIN4-scFv-S2 VL | ALTQPSSVSANPGETVEVTCSGDDSRYYGWYQQKSPGSAPVTIYYNDK<br>RPSDIPSRFSGSKSGSTGTLTITGVQAEDEAVYFCGAYDSTTHSGSAFG<br>AGTTLTVL |
| 41 | NECTIN4-scFv-S6 VH | TVTLDESGGGLQTPGGGLSLVCKGSGFTFSSNGMAWVRQAPGKGLEFVA<br>GVNAAGSWTGYGAAVKGRATISRDNGQSTVRLQLNDLRAEDTGTYYCAK<br>-----TADDWY-GADDIDAWGHGTEVIVSS |
| 42 | NECTIN4-scFv-S6 VL | ALTQPSSVSTNLGETVEITCSGSSGYGYGWYQQKSPGSAPVTIYSNDK<br>RPSDIPSRFSGSASGSTATLTITVRAEDEAVYLCGGYDSSASYVGIFGA<br>GTTLTVL |
| 43 | NECTIN4-scFv-S8 VH | TVTLDESGGGLQTPGGGLSLVCKASGFTFNDYGMGWMRQAPGKGLEWVA<br>GISGSGSYTDYGAAVKGRAIISRDNGQSTVRLQLNNLRAEDTGTYVCAK<br>-----GSNSAYPDAADIDAWGHGTEVIVSS |
| 44 | NECTIN4-scFv-S8 VL | ALTQPSSVSANLGGTVEITCSGGSGYGYGWYQQKSPGSAPVTIYSNDK<br>RPSDIPSRFSGSASGSTATLTITGVRAEDEAVYFCGGYDSSASYVGIFG<br>AGTTLTVL |
| 45 | NECTIN4-scFv-S21 VH | AVTLDESGGGLQTPGGALSLVCKASGFTFSSYAMMWVRQAPGKGLEYIA<br>GIRSDGRYTYYGAAVKGRATISRDNGQSTVRLQLNNLRAEDTGTYYCAK<br>SGVTDTSSSTYSSASNIDAWGHGTEVIVSS |
| 46 | NECTIN4-scFv-S21 VL | ALTQPSSVSANLGGTVKITCSGGSG-SYGWYQQKSPGSAPVTLIYANTN<br>RPSDIPSRFSGSKSGSTSTLTITGVQAEDVAVYYCGSRDSS--YVGIFG<br>AGTTLTVL |

TABLE 1-continued

| SEQ ID NO | name | sequence |
|---|---|---|
| 47 | Short linker | GQSSRSS |
| 48 | Long linker 1 | GQSSRSSSGGGSSGGGGS |
| 49 | Long linker 2 | GQSSRSSGGGGSSGGGGS |
| 50 | Binding region of S21 | GELETSDVVTVVLGQDAKLPCFYRGDSGEQVGQVAWARVDAGEGAQELA LLHSKYGLHVSPAYEGRVEQPPPPRNPLDGSVLLRNAVQADEGEYECRV STFPAGSFQARLRLRV |

The antibody according to the disclosure can be full-length (for example, an IgG1 or IgG4 antibody) or may comprise only an antigen-binding portion (for example, a Fab, F(ab')$_2$ or scFv fragment), and may be modified to affect functionality as needed.

Various techniques known to persons of ordinary skill in the art can be used to determine whether an antibody "specifically binds to one or more amino acids" within a polypeptide or protein. Exemplary techniques include, e.g., routine cross-blocking assay such as that described in Antibodies, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody specifically binds is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267(2):252-259; Engen and Smith (2001) Anal. Chem. 73:256A-265A.

One can easily determine whether an antibody specifically binds to the same epitope as, or competes for binding with, a reference anti-nectin-4 antibody, by using routine methods known in the art. For example, to determine if a test antibody binds to the same epitope as a reference anti-nectin-4 antibody of the disclosure, the reference antibody is allowed to bind to a nectin-4 protein. Next, the ability of a test antibody to bind to the nectin-4 molecule is assessed. If the test antibody is able to bind to nectin-4 following saturation binding with the reference anti-nectin-4 antibody, it can be concluded that the test antibody binds to a different epitope than the reference anti-nectin-4 antibody. On the other hand, if the test antibody is not able to bind to the nectin-4 molecule following saturation binding with the reference anti-nectin-4 antibody, then the test antibody may bind to the same epitope as the epitope bound by the reference anti-nectin-4 antibody of the disclosure. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present disclosure, two antibodies bind to the same (or overlapping) epitope if, e.g., a 1-, 5-, 10-, 20- or 100-fold excess of one antibody inhibits binding of the other by at least 50%, but preferably 75%, 90% or even 99% as measured in a competitive binding assay. Alternatively, two antibodies are deemed to bind to the same epitope if essentially all amino acid mutations in the antigen that reduce or eliminate binding of one antibody, reduce or eliminate binding of the other. Two antibodies are deemed to have "overlapping epitopes" if only a subset of the amino acid mutations that reduce or eliminate binding of one antibody, reduce or eliminate binding of the other.

The antibody also includes an antigen-binding fragment of a full antibody molecule. An antigen-binding fragment of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of an antigen-binding fragment includes: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody typically comprises at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_{H1}$; (ii) $V_H$-$C_{H2}$; (iii) $V_H$-$C_{H3}$; (iv) $V_H$-$C_{H1}$-$C_{H2}$; (v) $V_H$-$C_{H1}$-$C_{H2}$-$C_{H3}$; (vi) $V_H$-$C_{H2}$-$C_{H3}$; (vii) $V_H$-$C_L$; (viii) $V_L$-$C_{H1}$; (ix) $V_L$-$C_{H2}$; (x) $V_L$-$C_{H3}$; (xi) $V_L$-$C_{H1}$-$C_{H2}$; (xii) $V_L$-$C_{H1}$-$C_{H2}$-$C_{H3}$; (xiii) $V_L$-$C_{H2}$-$C_{H3}$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domains (e.g., by disulfide bond(s)).

The anti-nectin-4 antibody disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes an antibody, and an antigen-binding fragment thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another mammalian germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired properties such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes an anti-nectin-4 antibody comprising variants of any of the $V_H$, $V_L$, and/or CDR amino acid sequences disclosed herein having one or more conservative substitutions. For example, the present disclosure includes an anti-nectin-4 antibody having $V_H$, $V_L$, and/or CDR amino acid sequences with, e.g., 10 or fewer, 8 or fewer, 6 or fewer, 4 or fewer, etc., conservative amino acid substitutions relative to any of the $V_H$, $V_L$, and/or CDR amino acid sequences disclosed herein.

In some embodiments of the disclosure, the antibody according to the disclosure is a humanized antibody. In order to improve the binding affinity of the humanized antibody according to the disclosure, some amino acid residues in the human framework region are replaced by the corresponding amino acid residues in the species of CDRs; e.g., a rodent.

The antibodies of the present disclosure may be mono-specific, bispecific, or multispecific. Multispecific antibodies may be specific for different epitopes of one target polypeptide or may contain antigen-binding domains specific for more than one target polypeptide. The anti-nectin-4 antibodies of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bispecific or a multispecific antibody with a second binding specificity. For example, the present disclosure includes bispecific antibodies wherein one arm of an immunoglobulin is specific for nectin-4 or a fragment thereof, and the other arm of the immunoglobulin is specific for a second therapeutic target or is conjugated to a therapeutic moiety.

In one embodiment of the disclosure, the antibody or antigen-binding fragment thereof is conjugated with a therapeutic agent.

In some embodiments of the disclosure, the therapeutic agent represents a cytostatic or cytotoxic agent or an isotope-chelating agent with corresponding radioisotopes. Examples of the cytostatic or cytotoxic agent include, without limitation, antimetabolites (e.g., fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, gemcitabine, capecitibine, azathioprine, cytosine methotrexate, trimethoprim, pyrimethamine, or pemetrexed); alkylating agents (e.g., cmelphalan, chlorambucil, busulfan, thiotepa, ifosfamide, carmustine, lomustine, semustine, streptozocin, dacarbazine, mitomycin C, cyclophosphamide, mechlorethamine, uramustine, dibromomannitol, tetranitrate, procarbazine, altretamine, mitozolomide, or temozolomide); alkylating-like agents (e.g., cisplatin, carboplatin, nedaplatin, oxaliplatin, satraplatin, or triplatin); DNA minor groove alkylating agents (e.g., duocarmycins such as CC-1065, and any analogs or derivatives thereof; pyrrolobenzodiazapenes, or any analogs or derivatives thereof); anthracyclines (e.g., daunorubicin, doxorubicin, epirubicin, idarubicin, or valrubicin); antibiotics (e.g., dactinomycin, bleomycin, mithramycin, anthramycin, streptozotocin, gramicidin D, mitomycins (e.g., mitomycin C); calicheamicins; antimitotic agents (including, e.g., maytansinoids (such as DM1, DM3, and DM4), auristatins (including, e.g., monomethyl auristatin E (MMAE) and monomethyl auristatin F (MMAF)), dolastatins, cryptophycins, vinca alkaloids (e.g., vincristine, vinblastine, vindesine, vinorelbine), taxanes (e.g., paclitaxel, docetaxel, or a novel taxane), tubulysins, and colchicines); topoisomerase inhibitors (e.g., irinotecan, topotecan, camptothecin, etoposide, teniposide, amsacrine, or mitoxantrone); HDAC inhibitor (e.g., vorinostat, romidepsin, chidamide, panobinostat, or belinostat); proteasome inhibitors (e.g., peptidyl boronic acids); as well as radioisotopes such as $At^{211}$, $I^{131}$, $I^{125}$, $Y^{90}$, $Re^{186}$, $Re^{188}$, $Sm^{153}$, $Bi^{212}$ or $^{213}$, $P^{32}$ and radioactive isotopes of Lu including $Lu^{177}$. Examples of the isotope-chelating agents include, without limitation, ethylenediaminetetraacetic acid (EDTA), diethylenetriamine-N,N,N',N",N"'-pentaacetate (DTPA), 1,4,7,10-tetraazacyclododecane-N,N',N",N"'-tetraacetate (DOTA), 1,4,7,10-tetrakis(2-hydroxypropyl)-1,4,7,10-tetraazacyclododecane (THP), triethylenetetraamine-N,N,N',N",N"',N""-hexaacetate (TTHA), 1,4,7,10-tetraazacyclododecane-N,N',N",N"'-tetrakis(methylenephosphonate) (DOTP), and mercaptoacetyltriglycine (MAG3).

In one embodiment of the disclosure, the antibody or antigen-binding fragment thereof is expressed on the surface of a cell. Particularly, the cell is a T-cell or a stem cell, such as an iPSC. Induced pluripotent stem cells can be reprogrammed by inducing Yamanaka factors into somatic cells. Being like embryonic stem cells, iPSCs have the ability to be differentiated into cells of three-germ layers without the ethical concerns. With this property, iPSCs exhibit promising applications for clinical use.

In some embodiments of the disclosure, the antibody or antigen-binding fragment thereof is in the form of a chimeric antigen receptor.

The term "chimeric antigen receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other, e.g., are in different polypeptide chains.

The antibody or antigen-binding fragment thereof may be encoded in a vector encoding the antibody or antigen-binding fragment thereof. An exemplary vector is a lentivirus vector. "Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

In another aspect, the present disclosure provides a genetically engineered cell expressing the antibody or antigen-binding fragment thereof or containing the vector. The genetically engineered cell may be an immune cell or a stem cell. Also, the present disclosure provides an immune cell, which is differentiated from the genetically engineered cell.

The disclosure provides pharmaceutical compositions comprising the antibody or antigen-binding fragment thereof, genetically engineered cell or immune cell of the present disclosure. The pharmaceutical compositions of the disclosure are formulated with suitable diluents, carriers, excipients, and other agents that provide improved transfer, delivery, tolerance, and the like. The compositions may be formulated for specific uses, such as for veterinary uses or pharmaceutical uses in humans. The form of the composition and the excipients, diluents and/or carriers used will depend upon the intended uses of the antibody and, for therapeutic uses, the mode of administration. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present disclosure is used for treating a condition or disease associated with EPHA10 in an adult patient, it may be advantageous to intravenously administer the antibody of the present disclosure. Depending on the severity of the condition, the frequency and the duration of the treatment can be adjusted. Effective dosages and schedules for administering the antibody may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once the entire pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

In another aspect, the present disclosure provides a method of detecting or diagnosing whether a subject has, or is at risk of developing a tumor, or assessing a prognosis of a tumor, comprising contacting a sample derived from the subject with the antibody or antigen-binding fragment thereof.

The present disclosure provides a method for detecting nectin-4 in a sample comprising contacting the sample with the antibody or antigen-binding fragment thereof.

The present disclosure also provides a kit for detecting nectin-4 in a sample, wherein the kit comprises the antibody or antigen-binding fragment thereof.

In another aspect, the present disclosure provides a method for treating, prophylactic treating and/or preventing a tumor in a subject afflicted with the tumor, comprising administering to the subject the pharmaceutical composition. Alternatively, the present disclosure provides a pharmaceutical composition for use in treating, prophylactic treating and/or preventing a tumor in a subject afflicted with the tumor, comprising an effective amount of the antibody or antigen-binding fragment thereof or the genetically engineered cell as disclosed herein.

One example of cancers is solid tumors. Another example of cancers are liquid tumors such as lymphomas, leukemias, and hematological malignancies. Further examples of cancers of the disclosure include triple negative breast cancer, breast cancer, breast cancer metastases, metastases of any cancers described herein, colon cancer, colon cancer metastases, sarcomas, acute lymphoblastic leukemia, acute myeloid leukemia, adrenocortical carcinoma, AIDS-related cancers such as Kaposi sarcoma, AIDS-related lymphoma, primary CNS lymphoma, anal cancer, appendix cancer, childhood astrocytomas, astrocytomas, childhood atypical teratoid/rhabdiod tumor, CNS atypical teratoid/rhabdiod tumor, atypical teratoid/rhabdiod tumor, basal cell carcinoma, skin cancer, bile duct cancer, bladder cancer, bone cancer, Ewing sarcoma family of tumors, osteosarcoma, chondroma, chondrosarcoma, primary and metastatic bone cancer, malignant fibrous histiocytoma, childhood brain stem glioma, brain stem glioma, brain tumor, brain and spinal cord tumors, central nervous system embryonal tumors, childhood central nervous system embryonal tumors, central nervous system germ cell tumors, childhood central nervous system germ cell tumors, craniopharyngioma, childhood craniopharyngioma, ependymoma, childhood ependymoma, breast cancer, bronchial tumors, childhood bronchial tumors, burkitt lymphoma, carcinoid tumor, gastrointestinal cancer, carcinoma of unknown primary, cardiac tumors, childhood cardiac tumors, primary lymphoma, cervical cancer, cholangiocarcinoma, chordoma, childhood chordoma, chronic lymphocytic leukemia, chronic myelogenous leukemia, chronic myeloproliferative neoplasms, colon cancer, colorectal cancer, cutaneous T cell lymphoma, diffuse midline glioma, ductal carcinoma in situ, embryonal tumors, endometrial cancer, ependymoma, esophageal cancer, esthesioneuroblastoma, childhood esthesioneuroblastoma, ewing sarcoma, extracranial germ cell tumor, childhood extracranial germ cell tumor, extragonadal germ cell tumor, eye cancer, intraocular melanoma, retinoblastoma, fallopian tube cancer, fibrous histiocytoma of bone, gallbladder cancer, gastric cancer, gastrointestinal carcinoid tumor, gastrointestinal stromal tumors, ovarian cancer, testicular cancer, gestational trophoblastic disease, glioma, glioblastoma multiforme (GBM), low-grade glioma (LGG), gliomatosis cerebri, hairy cell leukemia, head and neck cancer, hepatocellular cancer, histiocytosis, Langerhans cell histiocytosis, hodgkin lymphoma, hypopharyngeal cancer, intraocular melanoma, melanoma, melanoma metastases, islet cell tumors, pancreatic neuroendocrine tumors, kidney cancer, renal cell tumors, Wilms tumor, childhood kidney tumors, lip and oral cavity cancer, liver cancer, lung cancer, medulloblastoma, nonhodgkin lymphoma, macroglodulinemia, Waldenstrom macroglodulinemia, male breast cancer, merkel cell carcinoma, metastatic squamous neck cancer with occult primary, midline tract carcinoma involving NUT gene, mouth cancer, multiple endocrine neoplasia syndromes, childhood multiple endocrine neoplasia syndromes, multiple myeloma/plasma cell neoplasm, mycosis fungoides, myelodysplastic syndromes, myelodysplastic/myeloproliferative neoplasms, multiple myeloma, myloproliferative neoplasms, chronic myeloproliferative neoplasms, myxopapillary ependymoma, nasal cavity and paranasal sinus cancer, nasopharyngeal cancer, neuroblastoma, non-small cell lung cancer, oligodendroglioma, oligoastrocytoma, oropharyngeal cancer, ovarian cancer, low malignant potential tumor, pancreatic cancer, pancreatic neuroendocrine tumors, papillomatosis, childhood papillomatosis, paraganglioma, paranasal sinus and nasal cavity cancer, parathyroid cancer, penile cancer, pheochromocytoma, pharyngeal cancer, pilocytic astrocytoma, pituitary tumor, pleomorphic xanthoastrocytoma (PXA), pleuropulmonary blastoma, childhood pleuropulmonary blastoma, primary peritoneal cancer, prostate cancer, rectal cancer, pregnancy-related cancer, rhabdomyo sarcoma, childhood rhabdomyo sarcoma, salivary gland cancer, Sezary syndrome, small cell lung cancer, small intestine caner, soft tissue sarcoma, squamous cell carcinoma, testicular cancer, throat cancer, thymoma, thymic carcinoma, thyroid cancer, transitional cell cancer of the renal, pelvis, and ureter, uterine cancer, urethral cancer, endometrial cancer, uterine sarcoma, vaginal cancer, vascular tumors, and vulvar cancers.

Nectin-4 expresses in 61% of ductal breast carcinoma and 6% in lobular type. While not wishing to be limited by theory, it is believed that the association CEA/CA15.3/Nectin-4 allows to monitor 74% of the breast carcinoma compared to 67% with the association CEA/CA15.3. Nectin-4 also upregulates EMT, metastasis and WNT/β-Catenin pathway via Pi3k/Akt axis. Clinicopathological data show induced nectin-4 in breast tumor metastases to axillary lymph nodes. In another aspect, nectin-4 is a potential angiogenesis biomarkers in breast cancer stem cells. Nectin-4 ecto-domain physically interacts with integrin-β4 and activates the angiogenesis pathways. The interaction of nectin-4 and integrin-β4 promotes angiogenesis via the Src, PI3K, AKT, iNOS pathway but not by Phospho-Erk or NF-κβ pathways The following examples are provided to aid those skilled in the art in practicing the present disclosure.

EXAMPLES

Example 1: Expression and Purification of Recombinant PVRL4 Fragment Proteins and Anti-PVRL4 scFvs Antigen. Briefly, Nectin-4-Q95NY8 (PVRL4_HUMAN) gene fragments of PVRL4_342 (94-435, 342 bps, r342p), PVRL4_639 (94-732, 639 bps, r639p), PVRL4_864 (94-957, 864 bps, r864p) were constructed in pET-21a(+) plasmids and the resulting vectors were transformed into E. coli. The bacterial culture from single colony was grown in 5 ml LB medium containing ampicillin (50 μg/ml) at 37° C. overnight, diluted 100-fold in the same LB medium and further grown until the $OD_{600}$ reached between 0.4 and 0.8. To induce the PVRL4 protein expression, isopropyl-β-D-thiogalactopyranoside (IPTG) was added to a final concentration of 1.0 mM in the culture. The cell pellet was resuspended in His-binding buffer containing 6M urea and lysed by sonication. After centrifugation, the resulting cellular lysate was incubated with a $Ni^{2+}$-sepharose (GE™ Healthcare Life Science, Pittsburgh, PA, USA) to purify the recombinant PVRL4 fusion protein according to the manufacturer's instruction.

The protein products were analyzed with SDS-PAGE as shown in FIG. 1.

Animal immunization. Female white leghorn (Gallus domesticus) chickens were first immunized with 50 μg of purified his-PVRL4_342 or 20 μg of purified his-PVRL4_864 in 0.5 ml Freund's complete adjuvant (SIGMA™, USA) by an intramuscular injection. Three additional immunizations with 50 μg of his-PVRL4_342 at intervals of 7 or 8 days followed by one additional immunization with 30 μg of his-PVRL4_342 after 1 month were performed. Similarly, 2nd immunization with 25 μg of his-PVRL4_863, 3 rd immunization with 20 μg of his-PVRL4_863, and 4th immunization with 15 μg of his-PVRL4_863 at intervals of 7 days were performed. After each immunization, polyclonal IgY antibodies in egg yolk were partially purified and titrated by an enzyme-linked immunosorbent assay (ELISA) to determine the presence of humoral anti-PVRL4 immune response. The IgY antibodies were purified from the yolk using 10% Dextran sulphate. The purified IgY antibodies were dissolved in 5 ml of TBS containing 0.05% sodium azide and stored at −20° C.

Construction of scFv Antibody Libraries. Briefly, spleens harvested from chickens following the final immunization were placed immediately in Trizol for homogenization. Twenty μg of total RNA was reversely transcribed into the first-strand cDNA using a SuperScript RT kit (INVITROGEN™, USA). After amplification using chicken-specific primers, PCR products of heavy and light chain variable (VH and VL) regions were subjected to a second round of PCR to form full-length scFv fragments with a short linker (such as SEQ ID NO. 47) or long linker (SEQ ID No 48 or 49), which were further cloned into the pComb3X vector. Recombinant phage DNAs were transformed into E. coli ER2738 strain by electroporation. The production of recombinant phages was initiated by the addition of wild-type VCS-M13 helper phage, which were subsequently precipitated with 4% polyethylene glycol 8000 and 3% NaCl (w/v), and finally re-suspended in 1× phosphate-buffered saline.

Cell-based Phage Display Panning. 50 μl of phage library ($10^{12}$-$10^{13}$) and 150 μl of 1% BSA in PBS was stayed at 4° C. for 1 hr. 100 μl of $10^6$ BML01 cells and 80 μl of phage were stayed at room temperature for 30 mins twice for negative selection. Total supernatant was added with $10^6$ BML01-Nectin4 cells and stayed at 4° C. for 1 hr for positive selection. The mixture was washed with PBS for 5 to 8 times. The phage was eluted by incubating the cells with 100 μl of 0.2 M Glycine-HCl (pH 2.2) at room temperature for 10 mins. The supernatant was collected and neutralized with 15 μl of 1M Tris-HCl, pH 9.1.

The phage titer was determined and amplified with E. coli ER2738. The results of phage titer and amplification are shown in Table 2.

TABLE 2

| PFU/μl | Panning 1 | Amplify 1 | Panning 2 | Amplify 2 | Panning 3 |
| --- | --- | --- | --- | --- | --- |
| Long linker | $1 \times 10^2$ | $1 \times 10^{10}$ | $2.4 \times 10^3$ | $2 \times 10^{10}$ | $1.1 \times 10^4$ |
| Short linker | $1 \times 10^4$ | $4 \times 10^{10}$ | $1 \times 10^4$ | $2 \times 10^2$ | $2.99 \times 10^5$ |

ScFv sequence alignment with heavy chain and light chain variable region genes of chicken immunoglobulin is shown in FIGS. 2A and 2B.

Figure 3A:
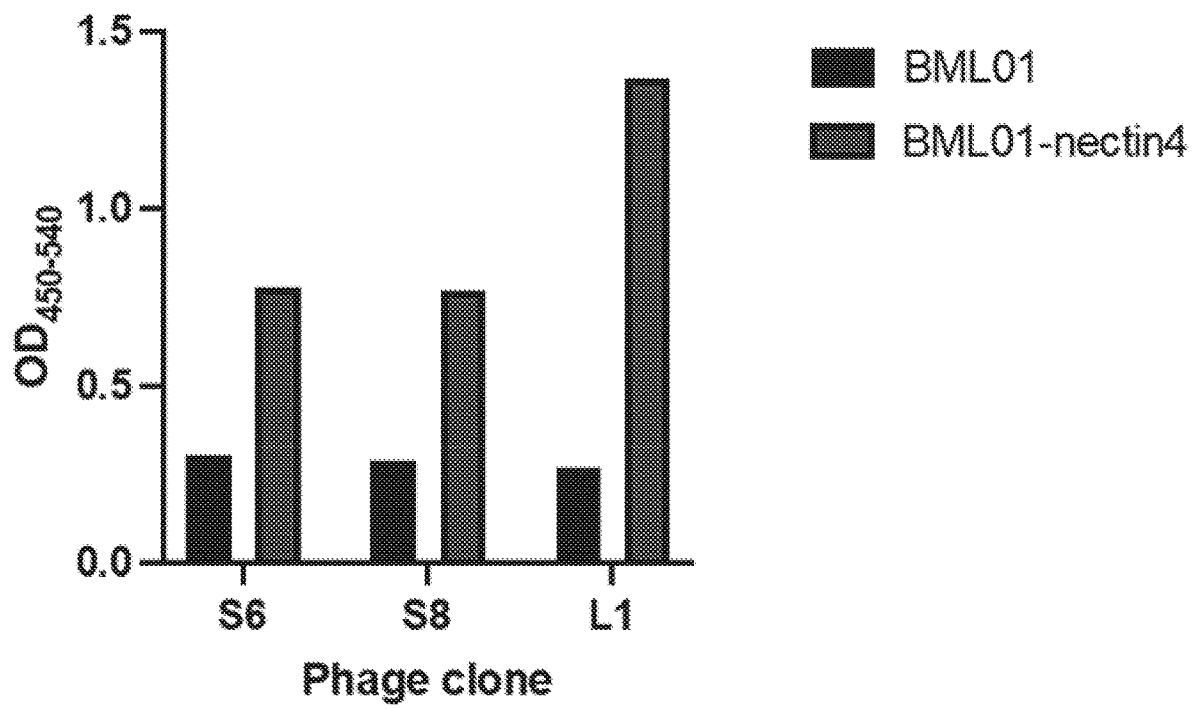
FIG. 3A shows affinity assay of anti-Nectin-4 M13 phage uses Nectin-4 expressed or not on BML01 cells.
Figure 3B:
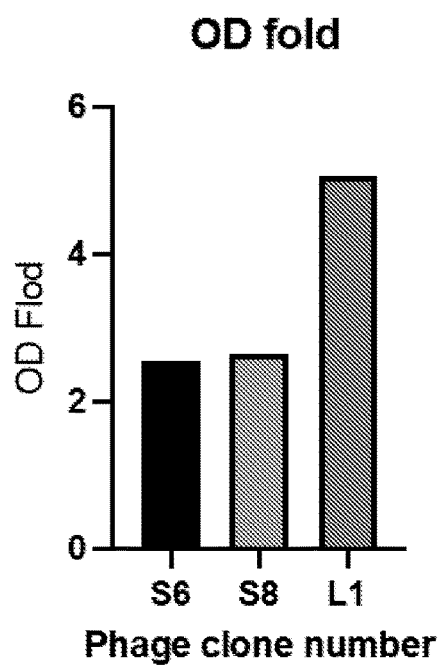
FIG. 3B shows Fold of affinity for anti-Nectin-4 M13 phage (BML01-nectin-4 $OD_{450}$/BML01 $OD_{450}$).

Cell-based ELISA. BML01 cells or Nectin 4-overexpressed BML01 cells were suspended in 10% FBS RPMI medium at $1 \times 10^6$ cell/ml. 100 μl of cells were seeded into a 96-well round-bottomed plate and added with 50 μl of candidate phage culture each well. The mixture was incubated at room temperature for 2 hours with shaking at 150 rpm and then washed with PBS for 3 times. The mixture was added with 100 μl of anti-M13-HRP (1:5000 dilution in 1% BSA in PBS) and incubated at room temperature for 2 hours with shaking at 150 rpm and then wash with PBS for 6 times. The mixture was added with 100 μl of TMB and then the reaction was stopped by adding 50 μl of 2N $H_2SO_4$. The results are shown in FIGS. 3A and 3B.

Figure 4:
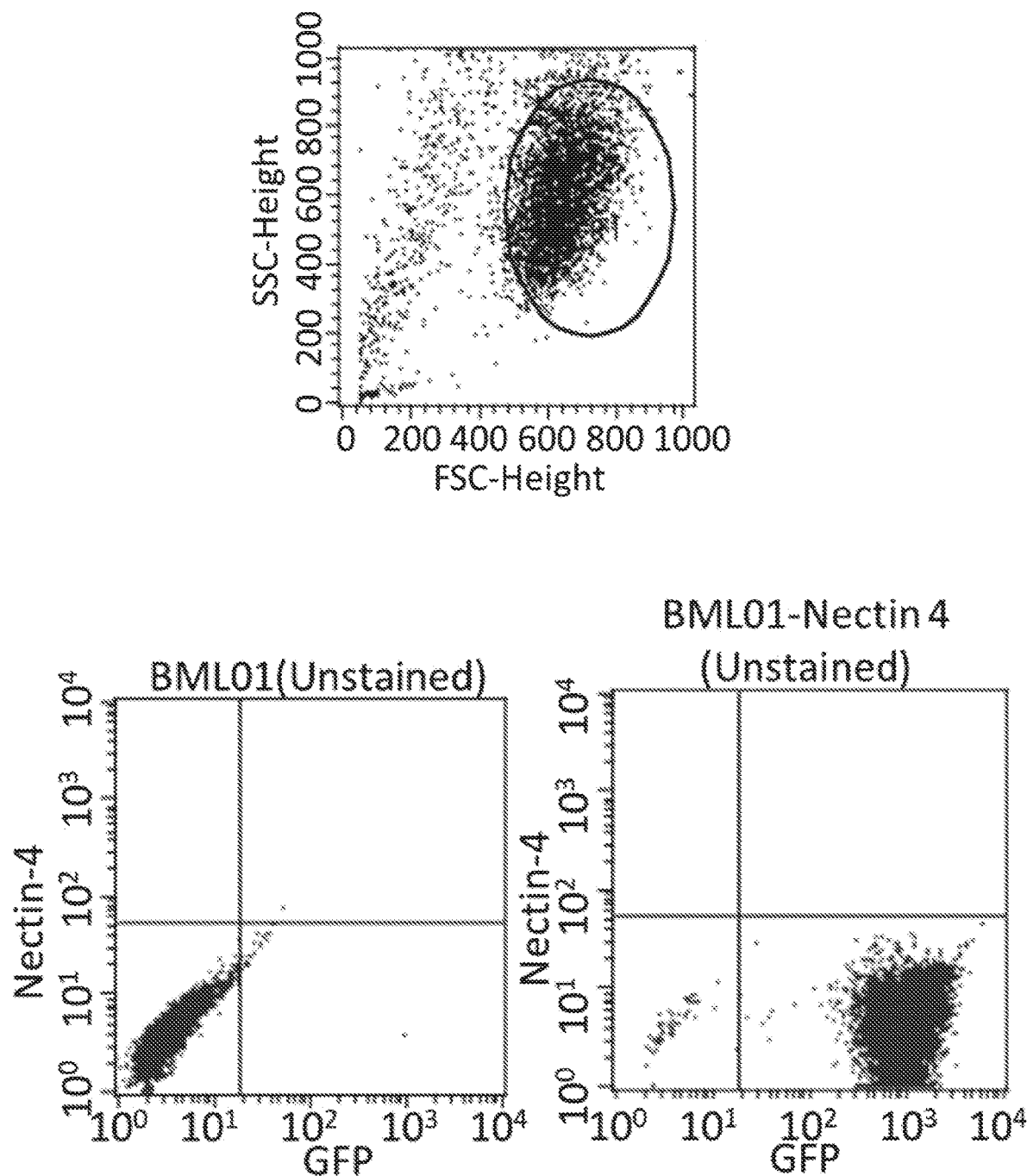
FIG. 4 shows the results of using anti-HA antibody to detect the binding activity of candidate phage clones.
Figure 4:
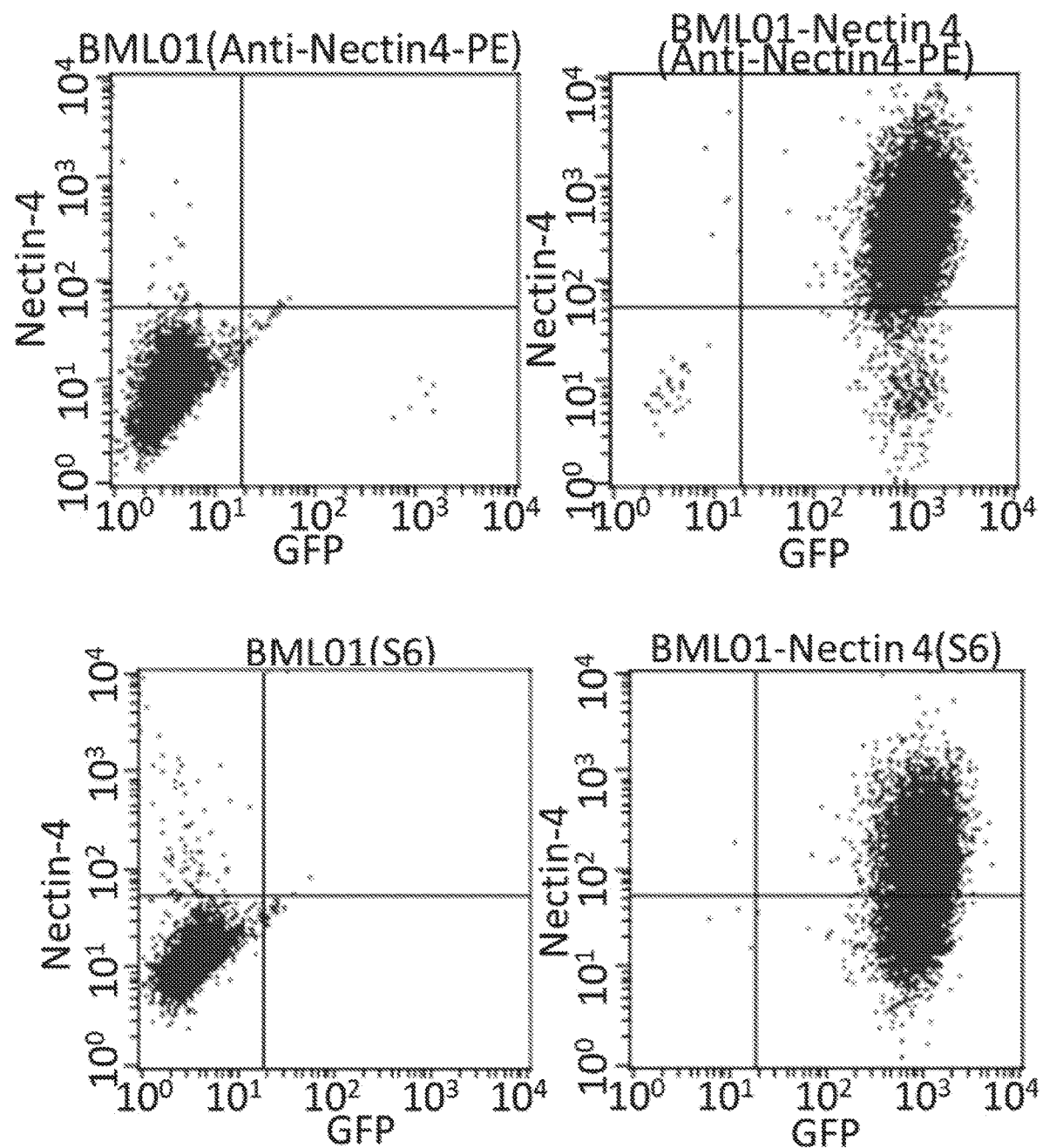
Figure 4:
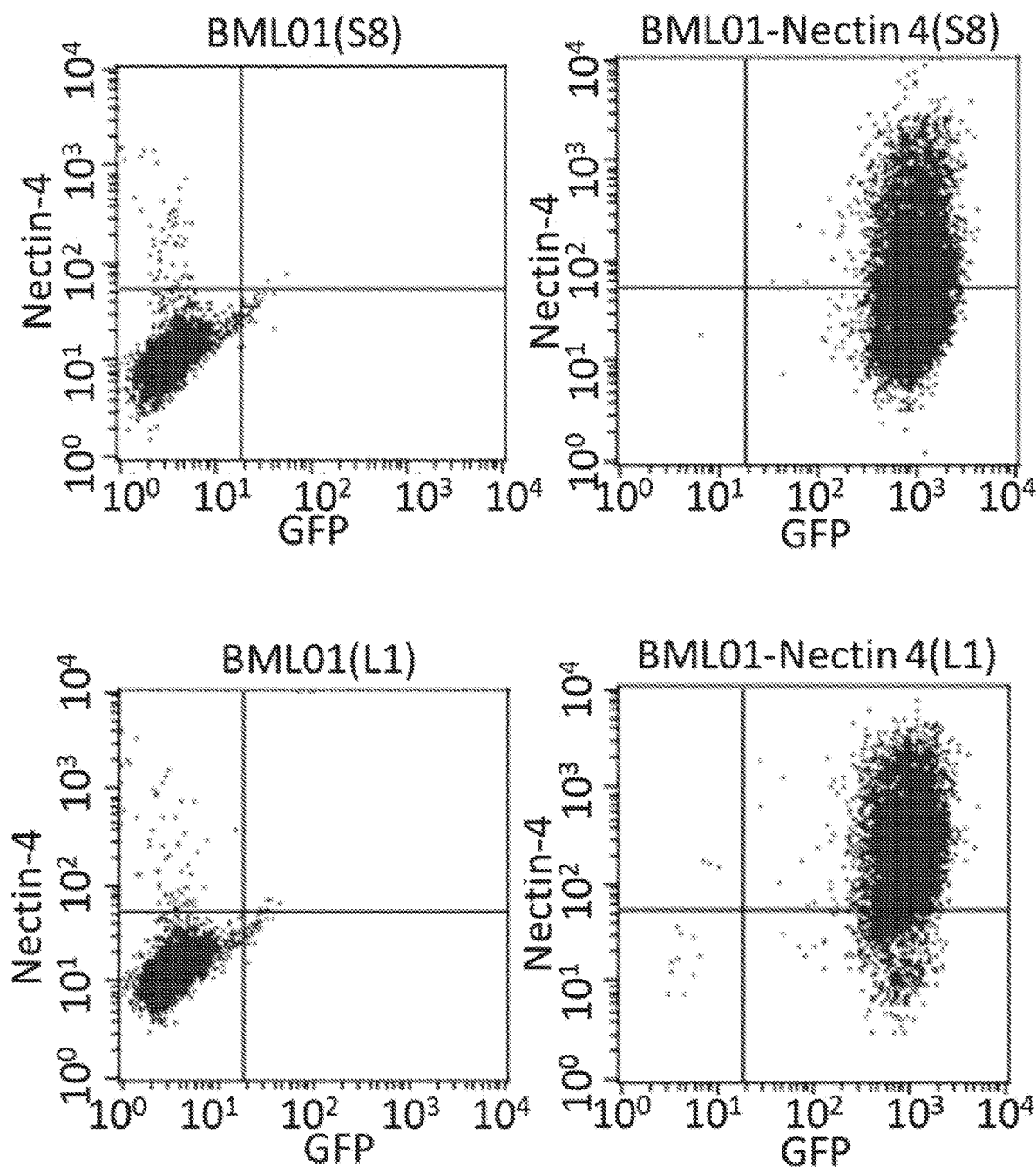

Anti-HA antibody was utilized to detect the binding activity of candidate phage clones. $1 \times 10^5$ cells in 100 μl of flow buffer was added with 20 μl of candidate phage clone and incubated at room temperature for 30 minutes and washed twice. Then anti-HA antibody was added and incubated at room temperature for 30 minutes and washed twice. The mixture was subjected to flow cytometry analysis and shown FIG. 4.

Figure 5:
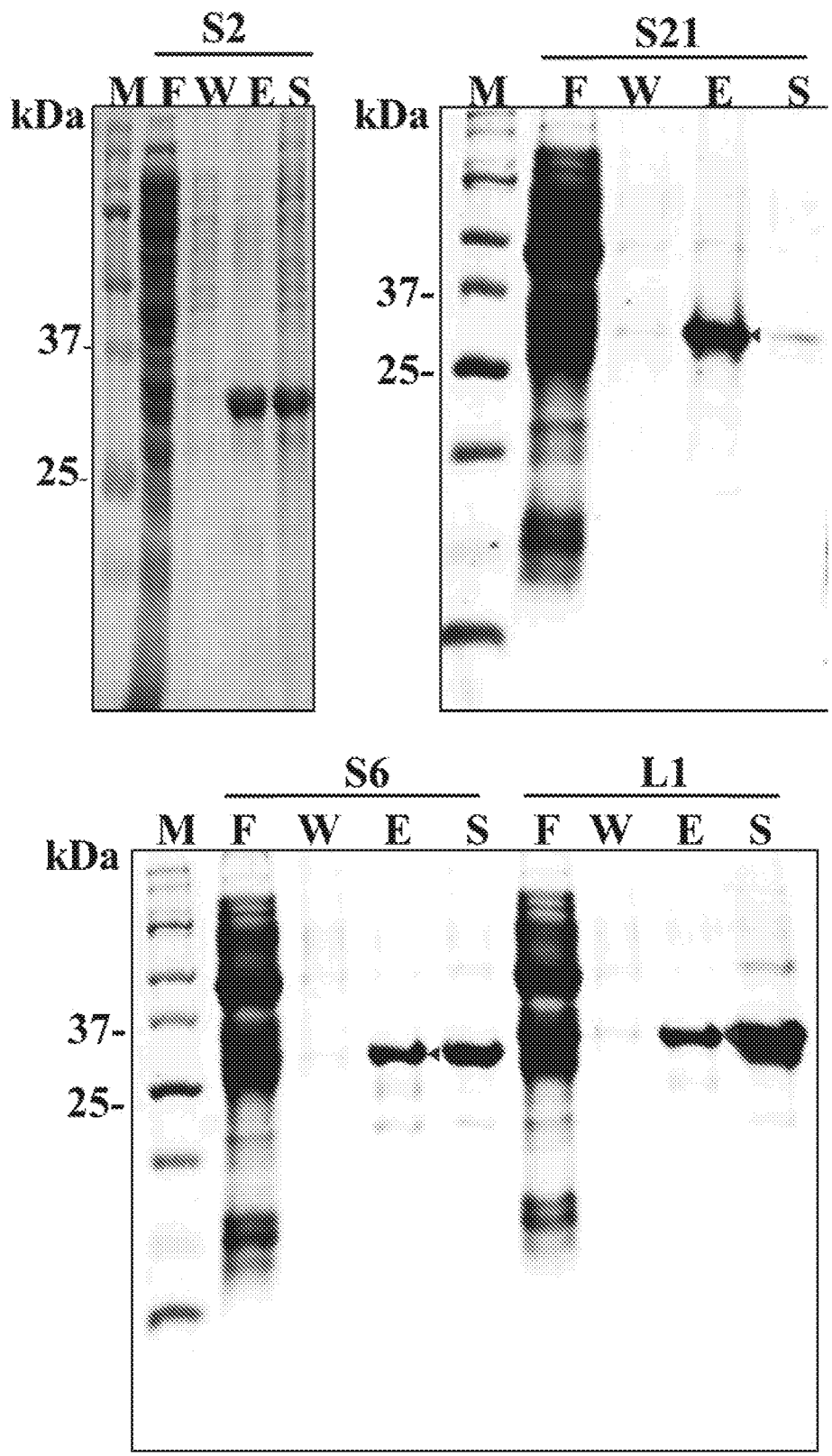
FIG. 5 shows protein expression of the scFvs.
Figure 6:
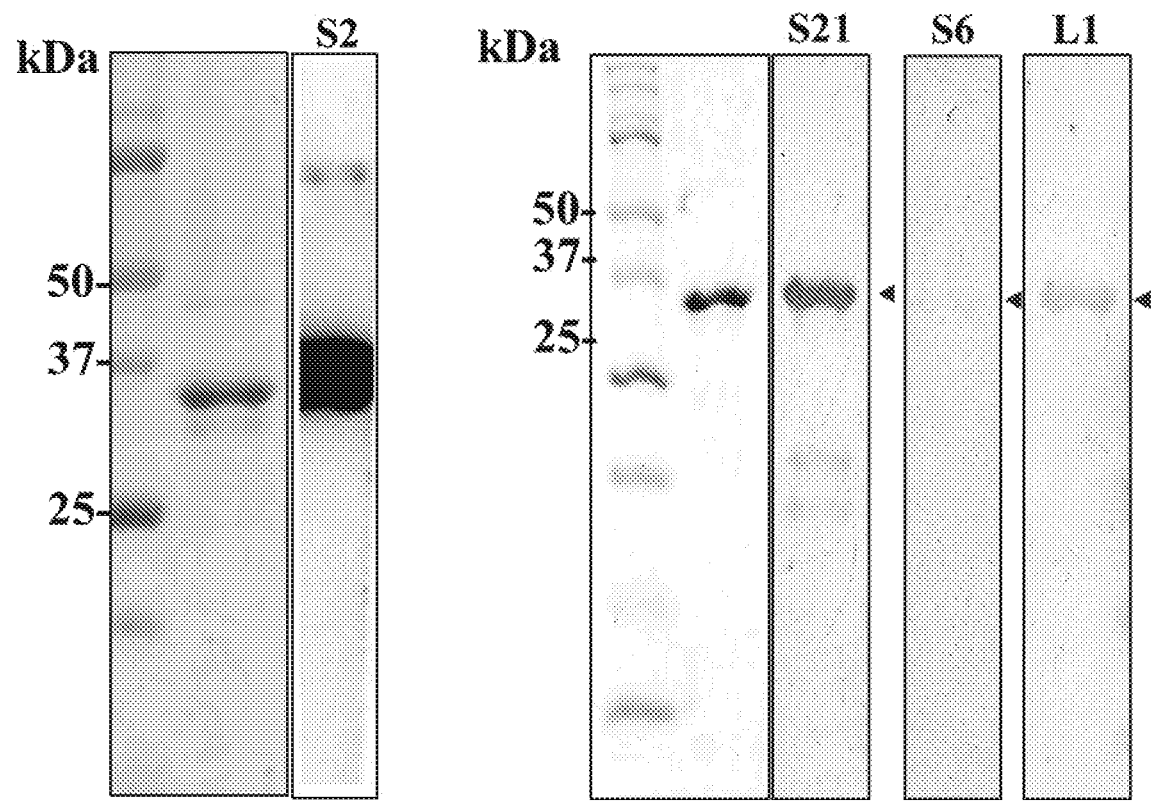
FIG. 6 shows binding ability of anti-PVRL4 scFvs against PVRL4 864 by western blotting.

Protein expression of the scFvs are shown in FIG. 5. Binding ability of anti-PVRL4 scFvs against PVRL4 864 was assayed by western blotting and shown in FIG. 6.

The binding ability of anti-PVRL4 scFvs with serial concentrations against PVRL4 864 and BSA was assayed with ELISA. The concentrations of the anti-PVRL4 scFVs at the OD450 nm value of 1 based on titration are shown in Table 3. It shows that S21 has the strongest affinity to PVRL4 864.

TABLE 3

| Ranking | Clone | Conc. (μg/ml) |
|---|---|---|
| 1 | S21 | 0.02 |
| 2 | L1 | 0.04 |
| 3 | L4 | 0.16 |
| 4 | S6 | 0.31 |

Figure 7:
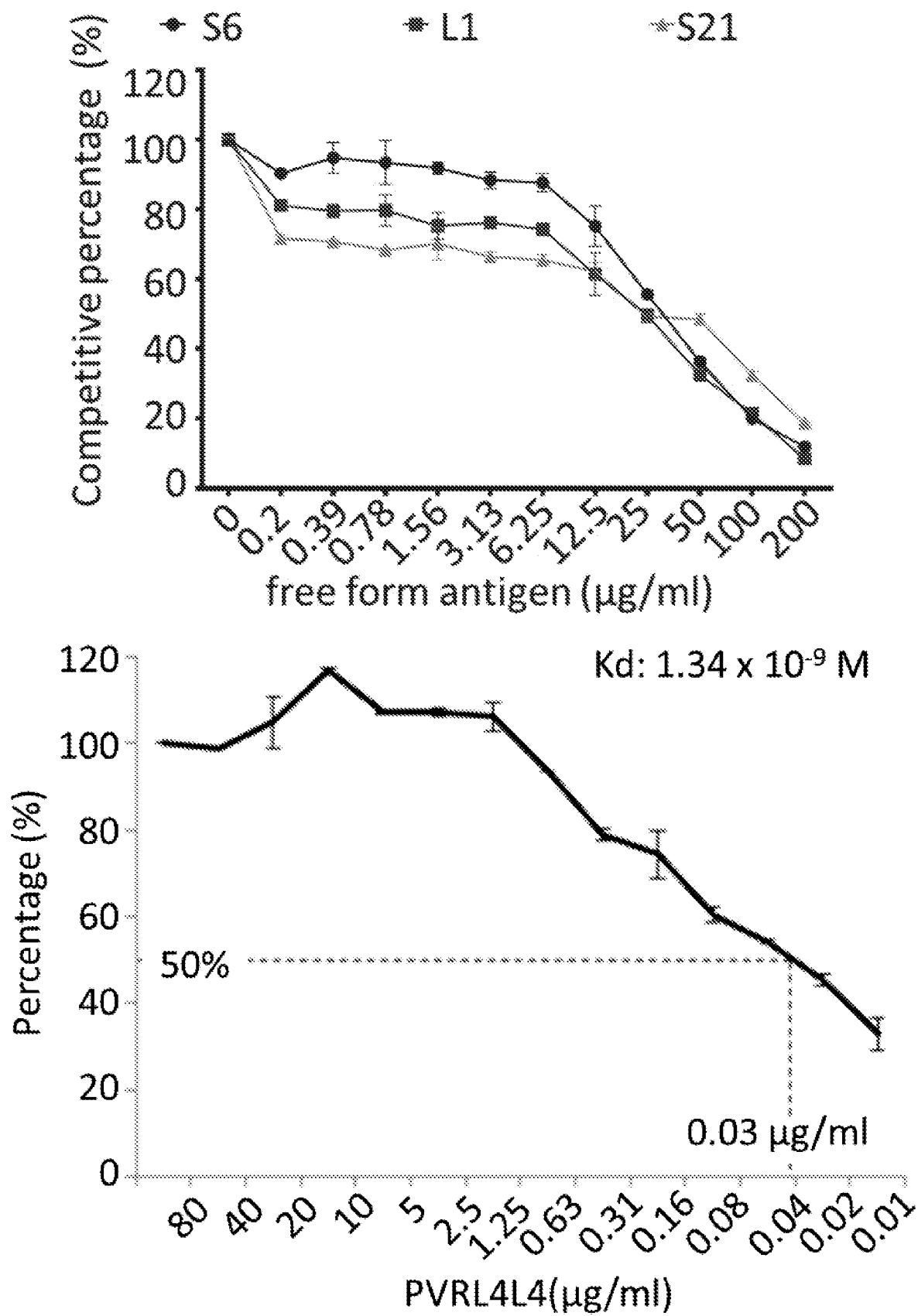
FIG. 7 shows the results of binding assay of L1/S6/S21/L4 against r864p by competitive ELISA or ELISA.

The results of binding assay of L1/S6/S21/L4 against r864p by competitive ELISA or ELISA is shown in FIG. 7. The first antibody is purified scFv; the second antibody is goat anti-chicken light chain (1:3000); the third antibody is HRC conjugated donkey anti-goat IgG antibody (1:5000). The $K_d$ value of anti-PVRL4 scFv are shown in Table 4.

| Clone | 50% concentration (μg/ml) | $K_d$ value (M) |
|---|---|---|
| L4(not by competitive ELISA) | 0.03 | $1.34 \times 10^{-9}$ |
| S21 | 52.47 | $1.41 \times 10^{-6}$ |
| S6 | 34.87 | $9.42 \times 10^{-7}$ |
| L1 | 34.74 | $9.39 \times 10^{-7}$ |

We succeeded in generating recombinant PVRL4 fragment proteins and anti-PVRL4_864 scFv.

Example 2: Characterization of Anti-PVRL4 scFvs

Figure 8:
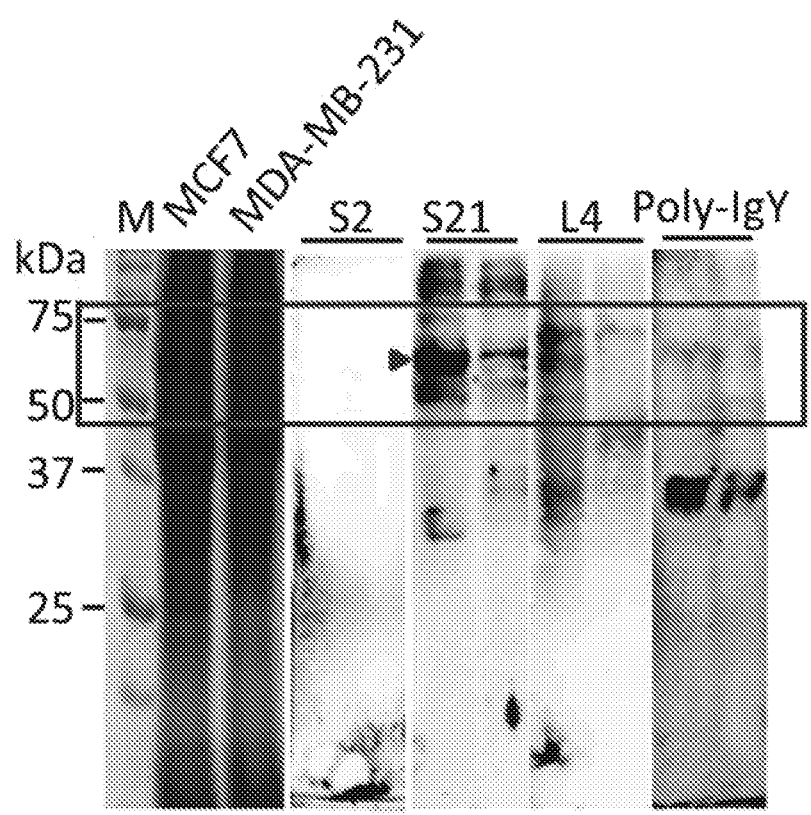
FIG. 8 shows binding ability of the monoclonal anti-PVRL4 scFvs on MCF-7 cells in Western blot analysis.

Binding ability of the monoclonal anti-PVRL4 scFvs on MCF-7 cells in Western blot analysis is shown in FIG. 8. MDA-MB-231 cells served as negative controls. The first antibody is purified scFvs S2, S21 and L4 (10 μg/ml); the second antibody is goat anti-chicken light chain (1:3000); the third antibody is HRP conjugated donkey anti-goat antibody (1:5000).

Figure 9A:
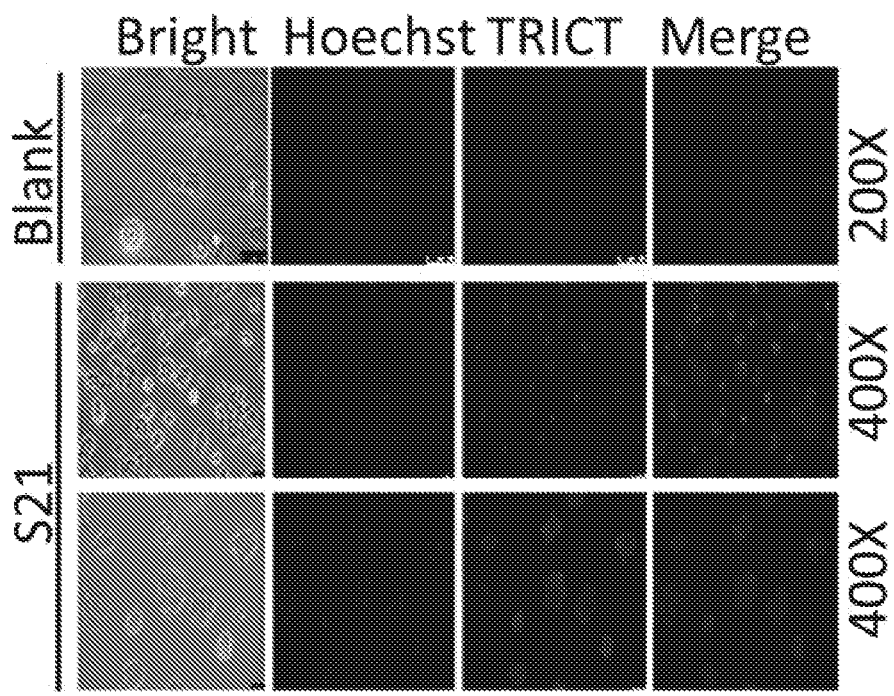
FIGS. 9A and 9B show the results of binding assay of anti-PVRL4 scFv against breast cancer cell line by immunofluorescence.
Figure 9B:
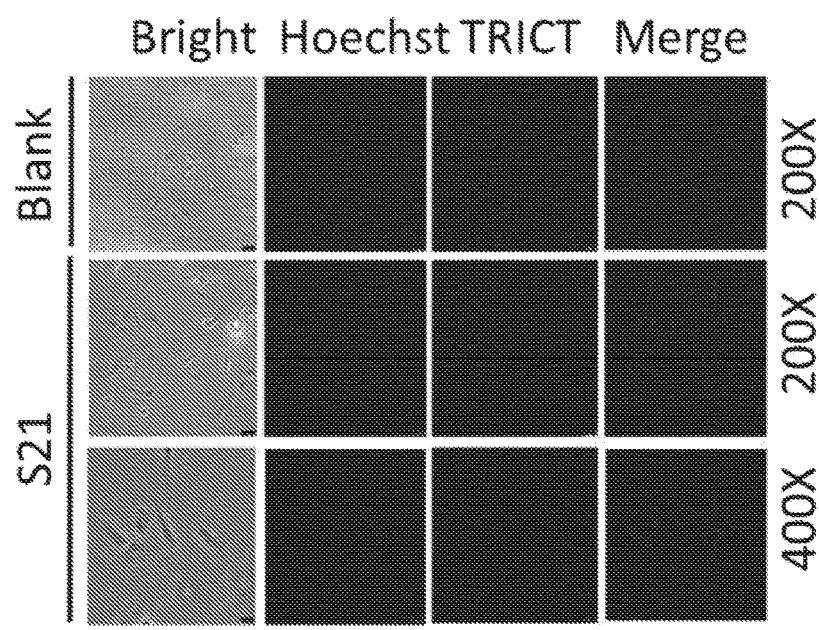
Figure 10:
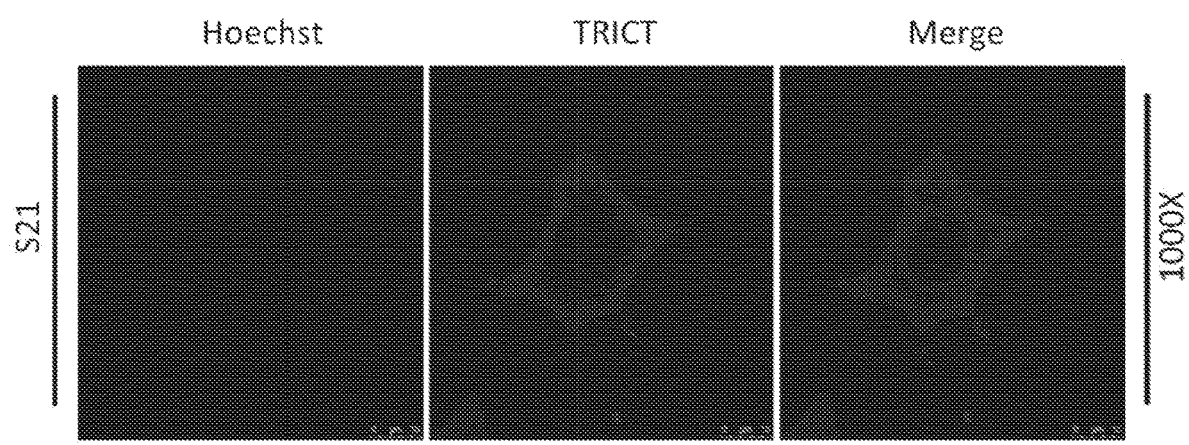
FIG. 10 shows the results of immunofluorescence staining of S21 against breast cancer cell line MCF7 on confocal microscopy.

The results of binding assay of anti-PVRL4 scFv against breast cancer cell line by immunofluorescence are shown in FIGS. 9A and 9B. The results of immunofluorescence staining of S21 against breast cancer cell line MCF7 on confocal microscopy are shown in FIG. 10. The first antibody is purified scFv S21 (300 μg/ml); the second antibody is goat anti-chicken light chain (1:400); the third antibody is TRIC conjugated rabbit anti-goat IgG antibody (1:400); blank is $2^{nd}$ and $3^{rd}$ antibodies without $1^{st}$ antibody.

Figure 11:
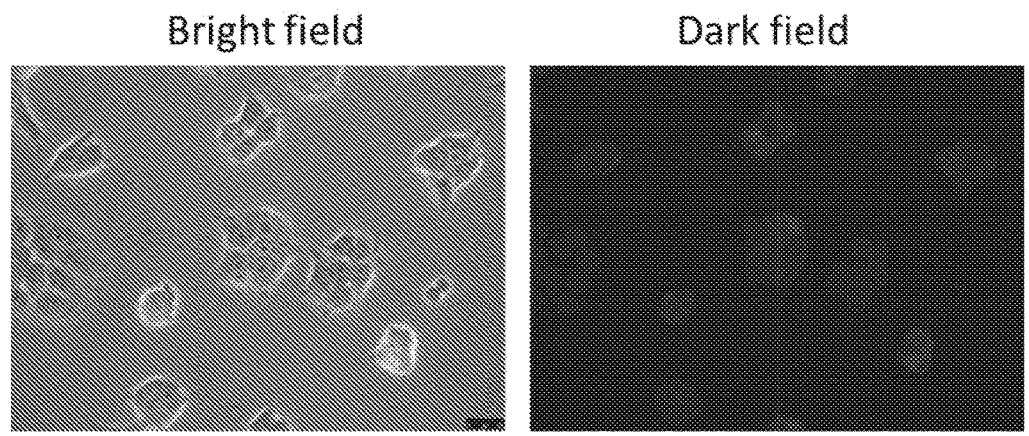
FIG. 11 shows the results of characterization of monoclonal anti-PVRL4 scFvs (S21) in staining assays.

The results of characterization of monoclonal anti-PVRL4 scFvs in staining assays are shown in FIG. 11. S21 was used for immunofluorescence staining (300 μg/ml) on MCF-7 cells and visualized with TRITC-conjugated antibody (400× magnification; representative data).

Figure 12:
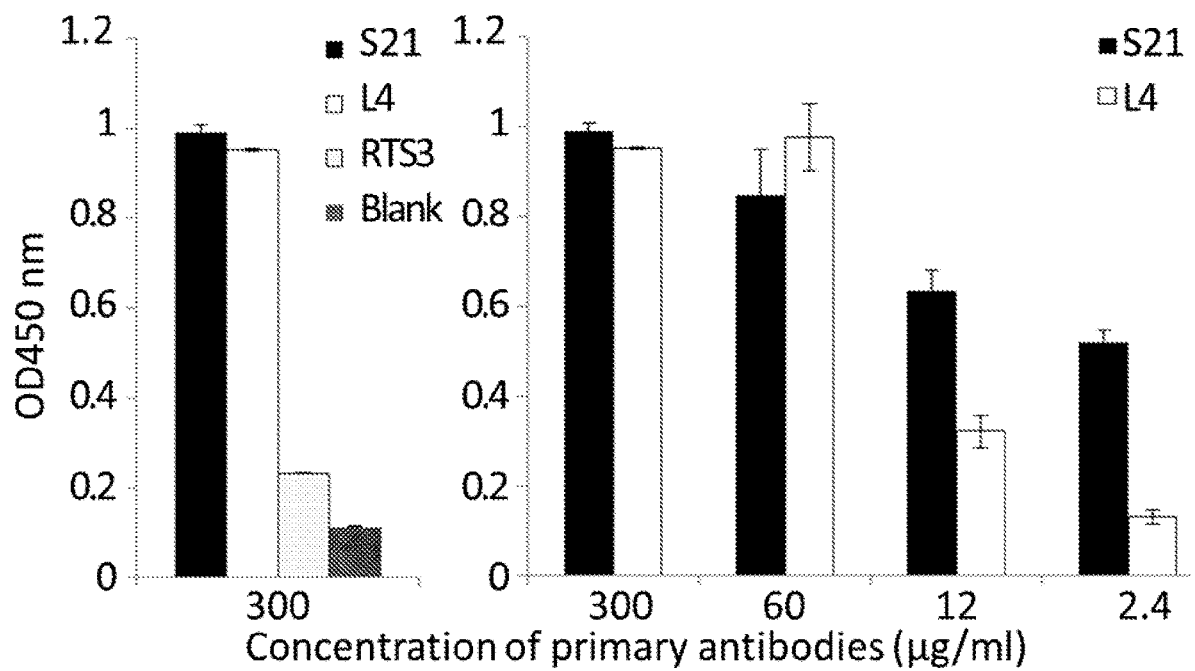
FIG. 12 shows binding ability of the monoclonal anti-PVRL4 scFvs on MCF-7 cells using ELISA (data shown as mean±SD, N=2).

The results of binding assay of anti-PVRL4 scFvs against breast cancer cell line MCF7 with cell ELISA are shown in FIG. 12. The first antibody is purified scFv S21 and L4 with series dilution; the second antibody is goat anti-chicken light chain (1:2000); the third antibody is HRC conjugated donkey anti-goat IgG antibody (1:4000); blank is $2^{nd}$ and $3^{rd}$ antibodies without $1^{st}$ antibody; negative control (NC) is anti-RT scFv S3 (RTS3).

Figure 13:
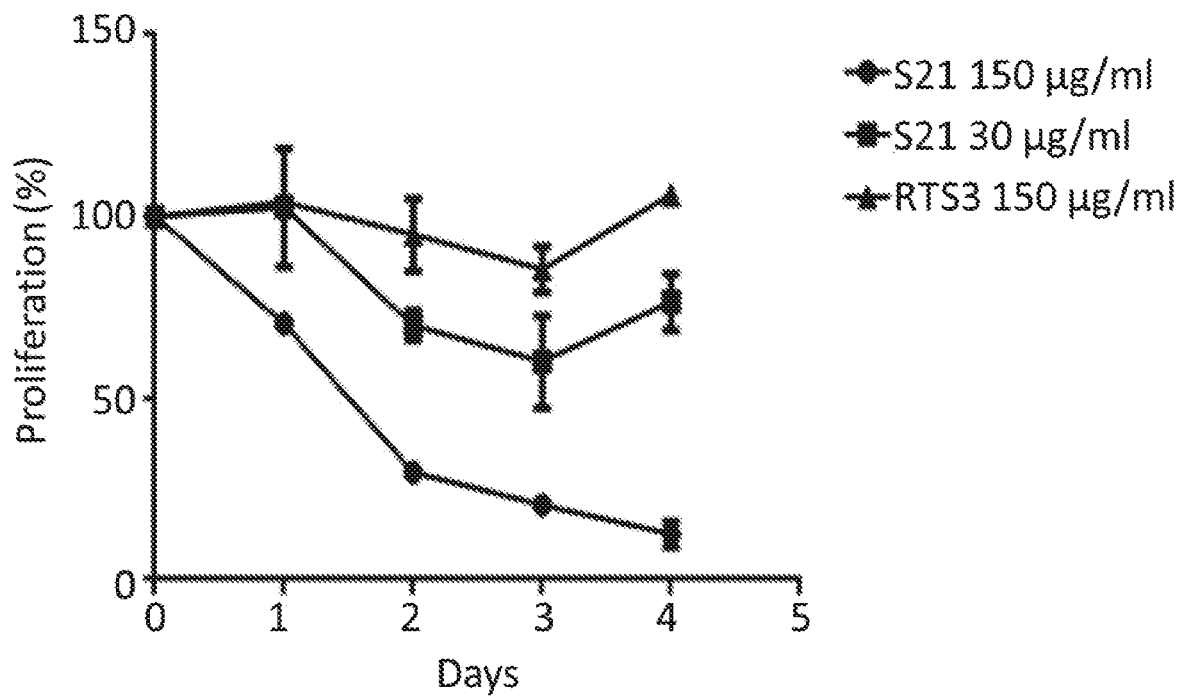
FIG. 13 shows the results of cell proliferation of MCF7 after treatment with anti-PVRL4 scFv S21.

The results of cell proliferation of MCF7 after treatment with anti-PVRL4 scFv S21 are shown in FIG. 13.

We found that the S21 may recognize the PVRL4 on MCF7 cell line and inhibit its proliferation.

Example 3: Epitope Mapping of PVRL4 with Anti-PVRL4 scFvs

Figure 14:
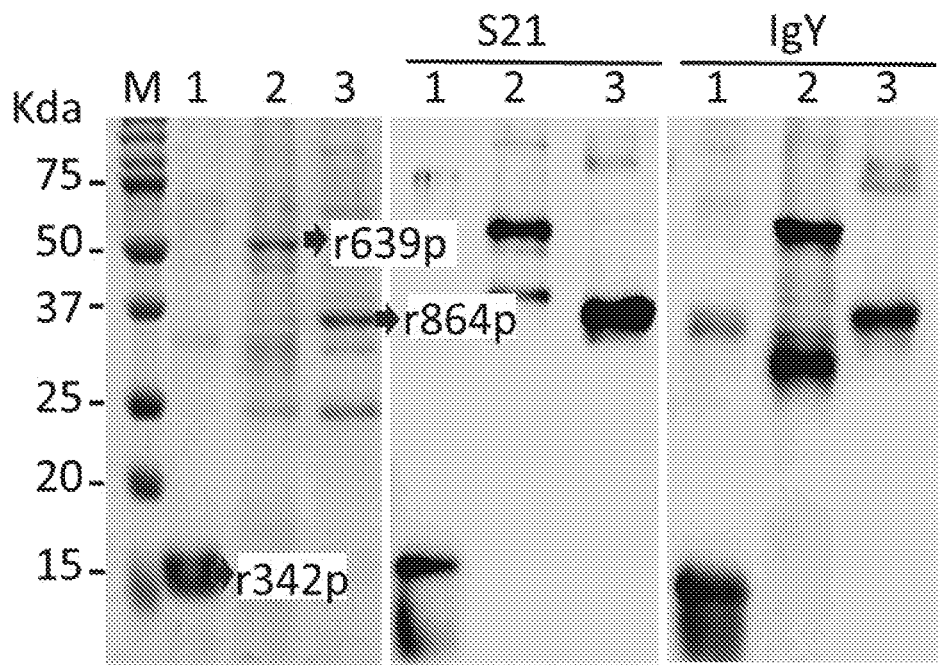
FIG. 14 shows the results of epitope mapping of anti-PVRL4 scFv S21.

The results of epitope mapping of anti-PVRL4 scFv S21 are shown in FIG. 14. The first antibody is purified scFv S21 (20 μg/ml) or anti-r864 $4^{th}$ immunized IgY (1:5000) as positive control; the second antibody is goat anti-chicken light chain (1:3000) or HRP conjugated donkey anti-chicken IgY (1:5000); the third antibody is HRC conjugated donkey anti-goat IgG antibody (1:5000). The binding region of S21 is SEQ ID NO: 50.

While the present disclosure has been described in conjunction with the specific embodiments set forth above, many alternatives thereto and modifications and variations thereof will be apparent to those of ordinary skill in the art. All such alternatives, modifications and variations are regarded as falling within the scope of the present disclosure.

What is claimed is:

1. An antibody or antigen-binding fragment thereof specific for an epitope on nectin cell adhesion molecule 4 (nectin-4) or a fragment thereof, which comprises complementarity determining regions (CDRs) of a heavy chain variable region and CDRs of a light chain variable region, wherein the CDRs of the heavy chain variable region comprises CDRH1, CDRH2 and CDRH3 regions, and the CDRs of the light chain variable region comprises CDRL1, CDRL2 and CDRL3 regions, and wherein:

the CDRH1 region comprises an amino acid sequence selected from the group consisting of SEQ ID NOs: 2 to 6; the CDRH2 region comprises an amino acid sequence selected from the group consisting of SEQ ID NOs: 8 to 12; and the CDRH3 region comprises an amino acid sequence selected from the group consisting of SEQ ID NOs: 14 to 18; and the CDRL1 region comprises an amino acid sequence selected from the group consisting of SEQ ID NOs: 20 to 24; the CDRL2 region comprises an amino acid sequence selected from the group consisting of SEQ ID NOs: 26 to 30; and the CDRL3 region comprises an amino acid sequence selected from the group consisting of SEQ ID NOs: 32 to 36.

2. The antibody or antigen-binding fragment thereof according to claim 1, wherein nectin-4 is human nectin-4.

3. The antibody or antigen-binding fragment thereof according to claim 1, which is specific for an epitope on an extracellular domain of nectin-4 or the fragment thereof.

4. The antibody or antigen-binding fragment thereof according to claim 1, which is specific for amino acids 94 to 435, 94 to 732, or 94 to 957 of nectin-4-Q96NY8 (PVRL4_HUMAN).

5. The antibody or antigen-binding fragment thereof according to claim 1, wherein the CDRH1 region comprises SEQ ID NO: 2, the CDRH2 region comprises SEQ ID NO: 8, the CDRH3 region comprises SEQ ID NO: 14, the CDRL1 region comprises SEQ ID NO: 20, the CDRL2 region comprises SEQ ID NO: 26, and the CDRL3 region comprises SEQ ID NO: 32;

the CDRH1 region comprises SEQ ID NO: 3, the CDRH2 region comprises SEQ ID NO: 9, the CDRH3 region comprises SEQ ID NO: 15, the CDRL1 region comprises SEQ ID NO: 21, the CDRL2 region comprises SEQ ID NO: 27, and the CDRL3 region comprises SEQ ID NO: 33;

the CDRH1 region comprises SEQ ID NO: 4, the CDRH2 region comprises SEQ ID NO: 10, the CDRH3 region comprises SEQ ID NO: 16, the CDRL1 region comprises SEQ ID NO: 22, the CDRL2 region comprises SEQ ID NO: 28, and the CDRL3 region comprises SEQ ID NO: 34;

the CDRH1 region comprises SEQ ID NO: 5, the CDRH2 region comprises SEQ ID NO: 11, the CDRH3 region comprises SEQ ID NO: 17, the CDRL1 region comprises SEQ ID NO: 23, the CDRL2 region comprises SEQ ID NO: 29, and the CDRL3 region comprises SEQ ID NO: 35; or the CDRH1 region comprises SEQ ID NO: 6, the CDRH2 region comprises SEQ ID NO: 12, the CDRH3 region comprises SEQ ID NO: 18, the CDRL1 region comprises SEQ ID NO: 24, the CDRL2 region comprises SEQ ID NO: 30, and the CDRL3 region comprises SEQ ID NO: 36.

6. The antibody or antigen-binding fragment thereof according to claim 1, wherein the heavy chain variable region comprises an amino acid sequence of SEQ ID NO: 37 or a substantially similar sequence having at least 90% sequence identity; and the light chain variable region comprises an amino acid sequence of SEQ ID NO: 38 or a substantially similar sequence having at least 90% sequence identity;

the heavy chain variable region comprises an amino acid sequence of SEQ ID NO: 39 or a substantially similar sequence having at least 90% sequence identity; and the light chain variable region comprises an amino acid sequence of SEQ ID NO: 40 or a substantially similar sequence having at least 90% sequence identity;

the heavy chain variable region comprises an amino acid sequence of SEQ ID NO: 41 or a substantially similar sequence having at least 90% sequence identity; and the light chain variable region comprises an amino acid sequence of SEQ ID NO: 42 or a substantially similar sequence having at least 90% sequence identity;

the heavy chain variable region comprises an amino acid sequence of SEQ ID NO: 43 or a substantially similar sequence having at least 90% sequence identity; and the light chain variable region comprises an amino acid sequence of SEQ ID NO: 44 or a substantially similar sequence having at least 90% sequence identity; or the heavy chain variable region comprises an amino acid sequence of SEQ ID NO: 45 or a substantially similar sequence having at least 90% sequence identity; and the light chain variable region comprises an amino acid sequence of SEQ ID NO: 46 or a substantially similar sequence having at least 90% sequence identity.

7. The antibody or antigen-binding fragment thereof according to claim 1, which is a monoclonal antibody, chimeric antibody, humanized antibody, human antibody, scFv antibody, or a fragment thereof.

8. The antibody or antigen-binding fragment thereof according to claim 1, which is conjugated with a therapeutic agent.

9. The antibody or antigen-binding fragment thereof according to claim 8, wherein the therapeutic agent is selected from the group consisting of antimetabolites, alkylating agents, alkylating-like agents, DNA minor groove alkylating agents, anthracyclines, antibiotics, calicheamicins, antimitotic agents, topoisomerase inhibitors, HDAC inhibitor, proteasome inhibitors, and radioisotopes.

10. The antibody or antigen-binding fragment thereof according to claim 1, which is expressed on a surface of a cell.

11. The antibody or antigen-binding fragment thereof according to claim 10, wherein the cell is an immune cell or a stem cell.

12. A vector encoding the antibody or antigen-binding fragment thereof according to claim 1.

13. A genetically engineered cell expressing the antibody or antigen-binding fragment thereof according to claim 1.

14. A kit for detecting nectin-4 in a sample, wherein the kit comprises the antibody or antigen-binding fragment thereof according to claim 1.

* * * * *

SEQUENCE LISTING

```
Sequence total quantity: 50
SEQ ID NO: 1              moltype = AA  length = 5
FEATURE                   Location/Qualifiers
source                    1..5
                          mol_type = protein
                          organism = Gallus domesticus
SEQUENCE: 1
SYDML                                                                     5

SEQ ID NO: 2              moltype = AA  length = 5
```

-continued

```
FEATURE                 Location/Qualifiers
source                  1..5
                        mol_type = protein
                        organism = Gallus domesticus
SEQUENCE: 2
SHGMF                                                                    5

SEQ ID NO: 3            moltype = AA  length = 5
FEATURE                 Location/Qualifiers
source                  1..5
                        mol_type = protein
                        organism = Gallus domesticus
SEQUENCE: 3
SNGMA                                                                    5

SEQ ID NO: 4            moltype = AA  length = 5
FEATURE                 Location/Qualifiers
source                  1..5
                        mol_type = protein
                        organism = Gallus domesticus
SEQUENCE: 4
SNGMA                                                                    5

SEQ ID NO: 5            moltype = AA  length = 5
FEATURE                 Location/Qualifiers
source                  1..5
                        mol_type = protein
                        organism = Gallus domesticus
SEQUENCE: 5
DYGMG                                                                    5

SEQ ID NO: 6            moltype = AA  length = 5
FEATURE                 Location/Qualifiers
source                  1..5
                        mol_type = protein
                        organism = Gallus domesticus
SEQUENCE: 6
SYAMM                                                                    5

SEQ ID NO: 7            moltype = AA  length = 17
FEATURE                 Location/Qualifiers
source                  1..17
                        mol_type = protein
                        organism = Gallus domesticus
SEQUENCE: 7
GIDNTGSYTH YGAAVKG                                                      17

SEQ ID NO: 8            moltype = AA  length = 17
FEATURE                 Location/Qualifiers
source                  1..17
                        mol_type = protein
                        organism = Gallus domesticus
SEQUENCE: 8
GISDAGSWTG YGAAVKG                                                      17

SEQ ID NO: 9            moltype = AA  length = 17
FEATURE                 Location/Qualifiers
source                  1..17
                        mol_type = protein
                        organism = Gallus domesticus
SEQUENCE: 9
GVNAAGSWTG YGAAVKG                                                      17

SEQ ID NO: 10           moltype = AA  length = 17
FEATURE                 Location/Qualifiers
source                  1..17
                        mol_type = protein
                        organism = Gallus domesticus
SEQUENCE: 10
GVNAAGSWTG YGAAVKG                                                      17

SEQ ID NO: 11           moltype = AA  length = 17
FEATURE                 Location/Qualifiers
source                  1..17
                        mol_type = protein
                        organism = Gallus domesticus
SEQUENCE: 11
GISGSGSYTD YGAAVKG                                                      17
```

```
SEQ ID NO: 12          moltype = AA   length = 17
FEATURE                Location/Qualifiers
source                 1..17
                       mol_type = protein
                       organism = Gallus domesticus
SEQUENCE: 12
GIRSDGRYTY YGAAVKG                                                  17

SEQ ID NO: 13          moltype = AA   length = 7
FEATURE                Location/Qualifiers
source                 1..7
                       mol_type = protein
                       organism = Gallus domesticus
SEQUENCE: 13
AKRTAGS                                                              7

SEQ ID NO: 14          moltype = AA   length = 12
FEATURE                Location/Qualifiers
source                 1..12
                       mol_type = protein
                       organism = Gallus domesticus
SEQUENCE: 14
AKSAGDWYGA DD                                                       12

SEQ ID NO: 15          moltype = AA   length = 12
FEATURE                Location/Qualifiers
source                 1..12
                       mol_type = protein
                       organism = Gallus domesticus
SEQUENCE: 15
AKTADDWYGA DD                                                       12

SEQ ID NO: 16          moltype = AA   length = 12
FEATURE                Location/Qualifiers
source                 1..12
                       mol_type = protein
                       organism = Gallus domesticus
SEQUENCE: 16
AKTADDWYGA DD                                                       12

SEQ ID NO: 17          moltype = AA   length = 13
FEATURE                Location/Qualifiers
source                 1..13
                       mol_type = protein
                       organism = Gallus domesticus
SEQUENCE: 17
AKGSNSAYPD AAD                                                      13

SEQ ID NO: 18          moltype = AA   length = 18
FEATURE                Location/Qualifiers
source                 1..18
                       mol_type = protein
                       organism = Gallus domesticus
SEQUENCE: 18
AKSGVTDTSS STYSSASN                                                 18

SEQ ID NO: 19          moltype = AA   length = 8
FEATURE                Location/Qualifiers
source                 1..8
                       mol_type = protein
                       organism = Gallus domesticus
SEQUENCE: 19
SGDSSYYG                                                             8

SEQ ID NO: 20          moltype = AA   length = 9
FEATURE                Location/Qualifiers
source                 1..9
                       mol_type = protein
                       organism = Gallus domesticus
SEQUENCE: 20
SGGSSNYYG                                                            9

SEQ ID NO: 21          moltype = AA   length = 9
FEATURE                Location/Qualifiers
source                 1..9
                       mol_type = protein
                       organism = Gallus domesticus
SEQUENCE: 21
SGDDSRYYG                                                            9
```

-continued

```
SEQ ID NO: 22            moltype = AA   length = 9
FEATURE                  Location/Qualifiers
source                   1..9
                         mol_type = protein
                         organism = Gallus domesticus
SEQUENCE: 22
SGSSGYGYG                                                                    9

SEQ ID NO: 23            moltype = AA   length = 9
FEATURE                  Location/Qualifiers
source                   1..9
                         mol_type = protein
                         organism = Gallus domesticus
SEQUENCE: 23
SGGSGYGYG                                                                    9

SEQ ID NO: 24            moltype = AA   length = 8
FEATURE                  Location/Qualifiers
source                   1..8
                         mol_type = protein
                         organism = Gallus domesticus
SEQUENCE: 24
SGGSGSYG                                                                     8

SEQ ID NO: 25            moltype = AA   length = 7
FEATURE                  Location/Qualifiers
source                   1..7
                         mol_type = protein
                         organism = Gallus domesticus
SEQUENCE: 25
DNTNRPS                                                                      7

SEQ ID NO: 26            moltype = AA   length = 7
FEATURE                  Location/Qualifiers
source                   1..7
                         mol_type = protein
                         organism = Gallus domesticus
SEQUENCE: 26
NNNKRPS                                                                      7

SEQ ID NO: 27            moltype = AA   length = 7
FEATURE                  Location/Qualifiers
source                   1..7
                         mol_type = protein
                         organism = Gallus domesticus
SEQUENCE: 27
YNDKRPS                                                                      7

SEQ ID NO: 28            moltype = AA   length = 7
FEATURE                  Location/Qualifiers
source                   1..7
                         mol_type = protein
                         organism = Gallus domesticus
SEQUENCE: 28
SNDKRPS                                                                      7

SEQ ID NO: 29            moltype = AA   length = 7
FEATURE                  Location/Qualifiers
source                   1..7
                         mol_type = protein
                         organism = Gallus domesticus
SEQUENCE: 29
SNDKRPS                                                                      7

SEQ ID NO: 30            moltype = AA   length = 7
FEATURE                  Location/Qualifiers
source                   1..7
                         mol_type = protein
                         organism = Gallus domesticus
SEQUENCE: 30
ANTNRPS                                                                      7

SEQ ID NO: 31            moltype = AA   length = 11
FEATURE                  Location/Qualifiers
source                   1..11
                         mol_type = protein
                         organism = Gallus domesticus
SEQUENCE: 31
```

```
ASTDSSSTAG I                                                                11

SEQ ID NO: 32           moltype = AA  length = 9
FEATURE                 Location/Qualifiers
source                  1..9
                        mol_type = protein
                        organism = Gallus domesticus
SEQUENCE: 32
GGWDKSAGI                                                                    9

SEQ ID NO: 33           moltype = AA  length = 12
FEATURE                 Location/Qualifiers
source                  1..12
                        mol_type = protein
                        organism = Gallus domesticus
SEQUENCE: 33
GAYDSTTHSG SA                                                               12

SEQ ID NO: 34           moltype = AA  length = 12
FEATURE                 Location/Qualifiers
source                  1..12
                        mol_type = protein
                        organism = Gallus domesticus
SEQUENCE: 34
GGYDSSASYV GI                                                               12

SEQ ID NO: 35           moltype = AA  length = 12
FEATURE                 Location/Qualifiers
source                  1..12
                        mol_type = protein
                        organism = Gallus domesticus
SEQUENCE: 35
GGYDSSASYV GI                                                               12

SEQ ID NO: 36           moltype = AA  length = 10
FEATURE                 Location/Qualifiers
source                  1..10
                        mol_type = protein
                        organism = Gallus domesticus
SEQUENCE: 36
GSRDSSYVGI                                                                  10

SEQ ID NO: 37           moltype = AA  length = 122
FEATURE                 Location/Qualifiers
source                  1..122
                        mol_type = protein
                        organism = synthetic construct
SEQUENCE: 37
AVTLDESGGG LQAPGGGLSL VCRASGFTFS SHGMFWVRQA PGKGLEFVAG ISDAGSWTGY            60
GAAVKGRATI SRDSGQSTVR LQLNNLRAED TGIYYCAKSA GDWYGADDID AWGHGTEVIV           120
SS                                                                         122

SEQ ID NO: 38           moltype = AA  length = 103
FEATURE                 Location/Qualifiers
source                  1..103
                        mol_type = protein
                        organism = synthetic construct
SEQUENCE: 38
ALTQPSSVSA NPGETVKITC SGGSSNYYGW YQQKSPGSAP VTLIYNNNKR PSDIPSRFSA            60
SKSGSTHTLT ITGVRAEDEA VYFCGGWDKS AGIFGAGTTL TVL                             103

SEQ ID NO: 39           moltype = AA  length = 122
FEATURE                 Location/Qualifiers
source                  1..122
                        mol_type = protein
                        organism = synthetic construct
SEQUENCE: 39
TVTLDESGGG LQTPGGGLSL VCKGSGFTFS SNGMAWVRQA PGKGLEFVGG VNAAGSWTGY            60
GAAVKGRATI SRDNGQSTVR LQLNDLRAED TGTYYCAKTA DDWYGADDID AWGHGTEVIV           120
SS                                                                         122

SEQ ID NO: 40           moltype = AA  length = 106
FEATURE                 Location/Qualifiers
source                  1..106
                        mol_type = protein
                        organism = synthetic construct
SEQUENCE: 40
ALTQPSSVSA NPGETVEVTC SGDDSRYYGW YQQKSPGSAP VTVIYYNDKR PSDIPSRFSG            60
SKSGSTGTLT ITGVQAEDEA VYFCGAYDST THSGSAFGAG TTLTVL                          106
```

```
SEQ ID NO: 41          moltype = AA  length = 122
FEATURE                Location/Qualifiers
source                 1..122
                       mol_type = protein
                       organism = synthetic construct
SEQUENCE: 41
TVTLDESGGG LQTPGGGLSL VCKGSGFTFS SNGMAWVRQA PGKGLEFVAG VNAAGSWTGY    60
GAAVKGRATI SRDNGQSTVR LQLNDLRAED TGTYYCAKTA DDWYGADDID AWGHGTEVIV   120
SS                                                                  122

SEQ ID NO: 42          moltype = AA  length = 106
FEATURE                Location/Qualifiers
source                 1..106
                       mol_type = protein
                       organism = synthetic construct
SEQUENCE: 42
ALTQPSSVST NLGETVEITC SGSSGYGYGW YQQKSPGSAP VTVIYSNDKR PSDIPSRFSG    60
SASGSTATLT ITGVRAEDEA VYLCGGYDSS ASYVGIFGAG TTLTVL                  106

SEQ ID NO: 43          moltype = AA  length = 123
FEATURE                Location/Qualifiers
source                 1..123
                       mol_type = protein
                       organism = synthetic construct
SEQUENCE: 43
TVTLDESGGG LQTPGGGLSL VCKASGFTFN DYGMGWMRQA PGKGLEWVAG ISGSGSYTDY    60
GAAVKGRAII SRDNGQSTVR LQLNNLRAED TGTYVCAKGS NSAYPDAADI DAWGHGTEVI   120
VSS                                                                 123

SEQ ID NO: 44          moltype = AA  length = 106
FEATURE                Location/Qualifiers
source                 1..106
                       mol_type = protein
                       organism = synthetic construct
SEQUENCE: 44
ALTQPSSVSA NLGGTVEITC SGGSGYGYGW YQQKSPGSAP VTVIYSNDKR PSDIPSRFSG    60
SASGSTATLT ITGVRAEDEA VYFCGGYDSS ASYVGIFGAG TTLTVL                  106

SEQ ID NO: 45          moltype = AA  length = 128
FEATURE                Location/Qualifiers
source                 1..128
                       mol_type = protein
                       organism = synthetic construct
SEQUENCE: 45
AVTLDESGGG LQTPGGALSL VCKASGFTFS SYAMMWVRQA PGKGLEYIAG IRSDGRYTYY    60
GAAVKGRATI SRDNGQSTVR LQLNNLRAED TGTYYCAKSG VTDTSSSTYS SASNIDAWGH   120
GTEVIVSS                                                            128

SEQ ID NO: 46          moltype = AA  length = 103
FEATURE                Location/Qualifiers
source                 1..103
                       mol_type = protein
                       organism = synthetic construct
SEQUENCE: 46
ALTQPSSVSA NLGGTVKITC SGGSGSYGWY QQKSPGSAPV TLIYANTNRP SDIPSRFSGS    60
KSGSTSTLTI TGVQAEDVAV YYCGSRDSSY VGIFGAGTTL TVL                     103

SEQ ID NO: 47          moltype = AA  length = 7
FEATURE                Location/Qualifiers
source                 1..7
                       mol_type = protein
                       organism = synthetic construct
SEQUENCE: 47
GQSSRSS                                                               7

SEQ ID NO: 48          moltype = AA  length = 18
FEATURE                Location/Qualifiers
source                 1..18
                       mol_type = protein
                       organism = synthetic construct
SEQUENCE: 48
GQSSRSSSGG GSSGGGGS                                                  18

SEQ ID NO: 49          moltype = AA  length = 18
FEATURE                Location/Qualifiers
source                 1..18
                       mol_type = protein
                       organism = synthetic construct
```

```
SEQUENCE: 49
GQSSRSSGGG GSSGGGGS                                                     18

SEQ ID NO: 50           moltype = AA  length = 114
FEATURE                 Location/Qualifiers
source                  1..114
                        mol_type = protein
                        organism = Homo sapiens
SEQUENCE: 50
GELETSDVVT VVLGQDAKLP CFYRGDSGEQ VGQVAWARVD AGEGAQELAL LHSKYGLHVS    60
PAYEGRVEQP PPPRNPLDGS VLLRNAVQAD EGEYECRVST FPAGSFQARL RLRV         114
```